(12) United States Patent
Rockwell et al.

(10) Patent No.: US 8,796,627 B2
(45) Date of Patent: Aug. 5, 2014

(54) APPARATUS AND METHOD FOR DETECTING THE PRESENCE OF WATER ON A REMOTE SURFACE

(75) Inventors: Thomas L. Rockwell, Rochester, NY (US); James E. Roddy, Rochester, NY (US)

(73) Assignee: Techwell Consulting LLC, Rochester, NY (US)

( * ) Notice: Subject to any disclaimer, the term of this patent is extended or adjusted under 35 U.S.C. 154(b) by 178 days.

(21) Appl. No.: 13/314,143

(22) Filed: Dec. 7, 2011

(65) Prior Publication Data

US 2012/0140233 A1    Jun. 7, 2012

Related U.S. Application Data

(60) Provisional application No. 61/459,125, filed on Dec. 7, 2010.

(51) Int. Cl.
*G01N 21/55* (2014.01)

(52) U.S. Cl.
CPC ..................................... *G01N 21/55* (2013.01)
USPC ..................................................... 250/341.8

(58) Field of Classification Search
CPC ...... G01N 21/55; G08B 21/20; G01F 23/292; G01S 17/00
USPC ........ 340/619, 605, 604, 603, 583; 250/341.8
See application file for complete search history.

(56) References Cited

U.S. PATENT DOCUMENTS

| | | |
|---|---|---|
| 3,471,698 A | 10/1969 | Mausteller et al. |
| 4,266,195 A | 5/1981 | Keefner et al. |
| 4,690,553 A | 9/1987 | Fukamizu et al. |
| 5,218,206 A | 6/1993 | Schmitt et al. |
| 5,406,082 A | 4/1995 | Pearson et al. |
| 5,652,655 A | 7/1997 | Uno et al. |
| 5,801,647 A | 9/1998 | Survo et al. |
| 5,818,339 A | 10/1998 | Giles et al. |
| 5,921,501 A | 7/1999 | Pernick |
| 5,962,853 A | 10/1999 | Huth-Fehre et al. |
| 6,040,916 A | 3/2000 | Griesinger |
| 6,049,387 A | 4/2000 | Griesinger |
| 6,079,433 A | 6/2000 | Saarem |
| 6,091,065 A | 7/2000 | Teder |
| 6,091,335 A | 7/2000 | Breda et al. |

(Continued)

OTHER PUBLICATIONS

Office Action dated Jun. 14, 2011 for U.S. Appl. No. 12/435,337, filed May 4, 2009.

(Continued)

*Primary Examiner* — Cconstantine Hannaher
(74) *Attorney, Agent, or Firm* — LeClairRyan, A Professional Corporation

(57) ABSTRACT

An apparatus is provided having a source for illuminating a remote surface with at least one wavelength of light (e.g., in the range of 940 to 970 nm), a detector for receiving returned illumination from the surface and providing an analog signal representative of the returned illumination, and a controller which samples the analog signal to obtain sample data representative of amplitude of light of the source returned from the surface by the detector. The controller determines the presence of water (or moisture, liquid, ice, vapor or heavy gases) on the surface in accordance with the sample data. An audible alarm is activatable by the controller. The source and detector are in a housing in perpendicular or non-perpendicular orientations with respect to the surface. Such housing being mountable at a distance from the surface where water detection is desired.

40 Claims, 24 Drawing Sheets

(56) References Cited

U.S. PATENT DOCUMENTS

| | | |
|---|---|---|
| 6,239,872 B1 * | 5/2001 | Wilt et al. .................. 250/341.8 |
| 6,414,598 B2 | 7/2002 | Freill et al. |
| 6,683,535 B1 | 1/2004 | Utke |
| 6,710,346 B2 * | 3/2004 | Brewington et al. ...... 250/341.8 |
| 6,794,650 B2 | 9/2004 | Burns et al. |
| 7,164,110 B2 | 1/2007 | Pitigoi-Aron et al. |
| 7,224,453 B2 | 5/2007 | Elman |
| 7,239,246 B2 | 7/2007 | Picco et al. |
| 7,269,954 B2 | 9/2007 | Haertel et al. |
| 7,306,008 B2 | 12/2007 | Tornay |
| 7,312,713 B2 | 12/2007 | Alfano et al. |
| 7,370,525 B1 | 5/2008 | Zhao et al. |
| 7,562,678 B1 | 7/2009 | Kulikov et al. |
| 7,696,889 B2 | 4/2010 | David |
| 8,248,256 B1 | 8/2012 | Gerardi |
| 2002/0011570 A1 | 1/2002 | Castleman |
| 2003/0080753 A1 | 5/2003 | Rains et al. |
| 2004/0024538 A1 | 2/2004 | Severson et al. |
| 2005/0047864 A1 | 3/2005 | Yamada et al. |
| 2005/0167593 A1 | 8/2005 | Forsyth |
| 2006/0005312 A1 | 1/2006 | Reddy et al. |
| 2007/0001864 A1 | 1/2007 | Gammon |
| 2007/0024458 A1 | 2/2007 | McGinty et al. |
| 2009/0032712 A1 | 2/2009 | Robert et al. |
| 2009/0201162 A1 | 8/2009 | Barth et al. |
| 2009/0224927 A1 | 9/2009 | Sudy et al. |

OTHER PUBLICATIONS

International Search Report for International Patent Application No. PCT/US2011/01966 (Apr. 13, 2012).

* cited by examiner

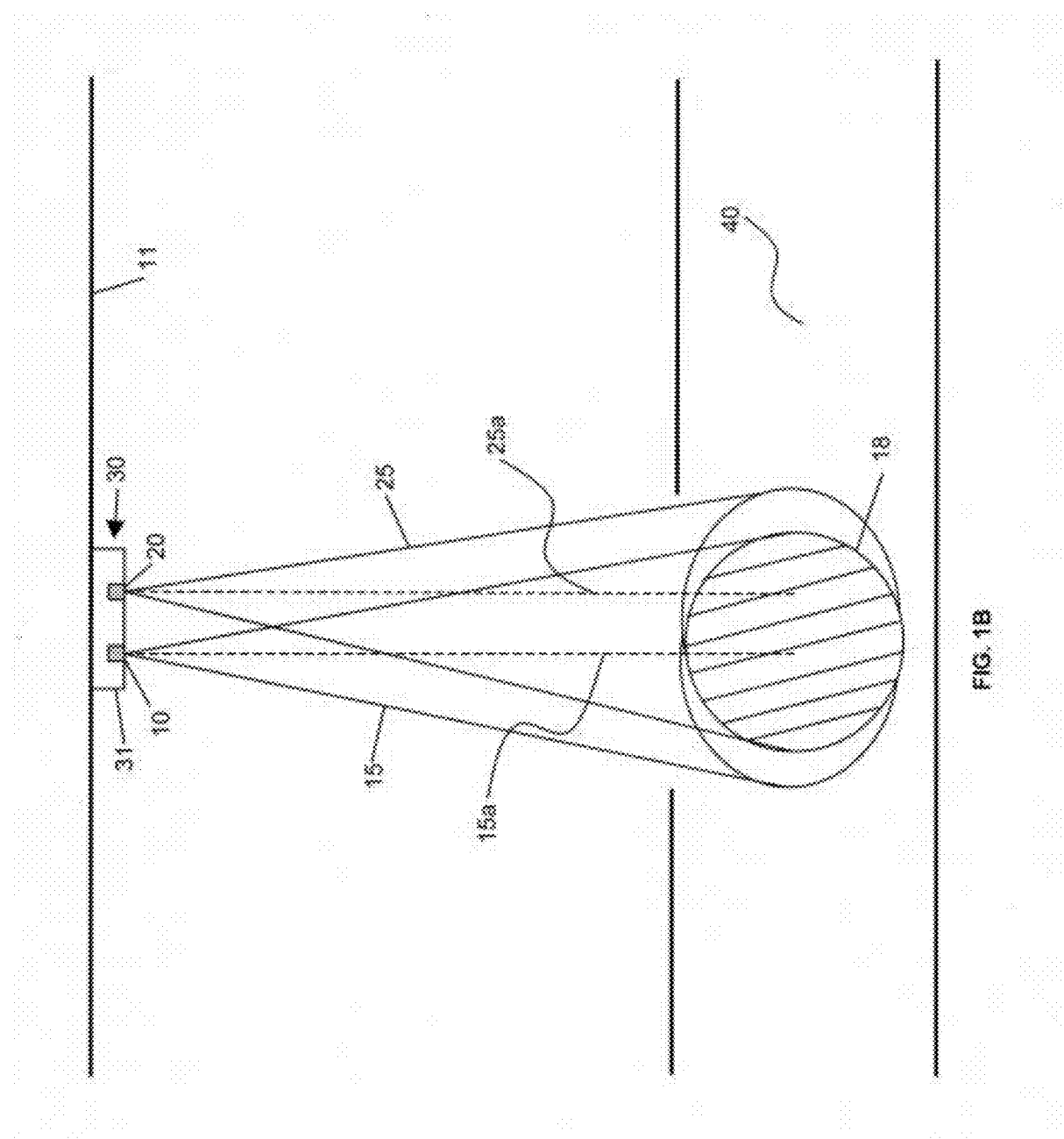

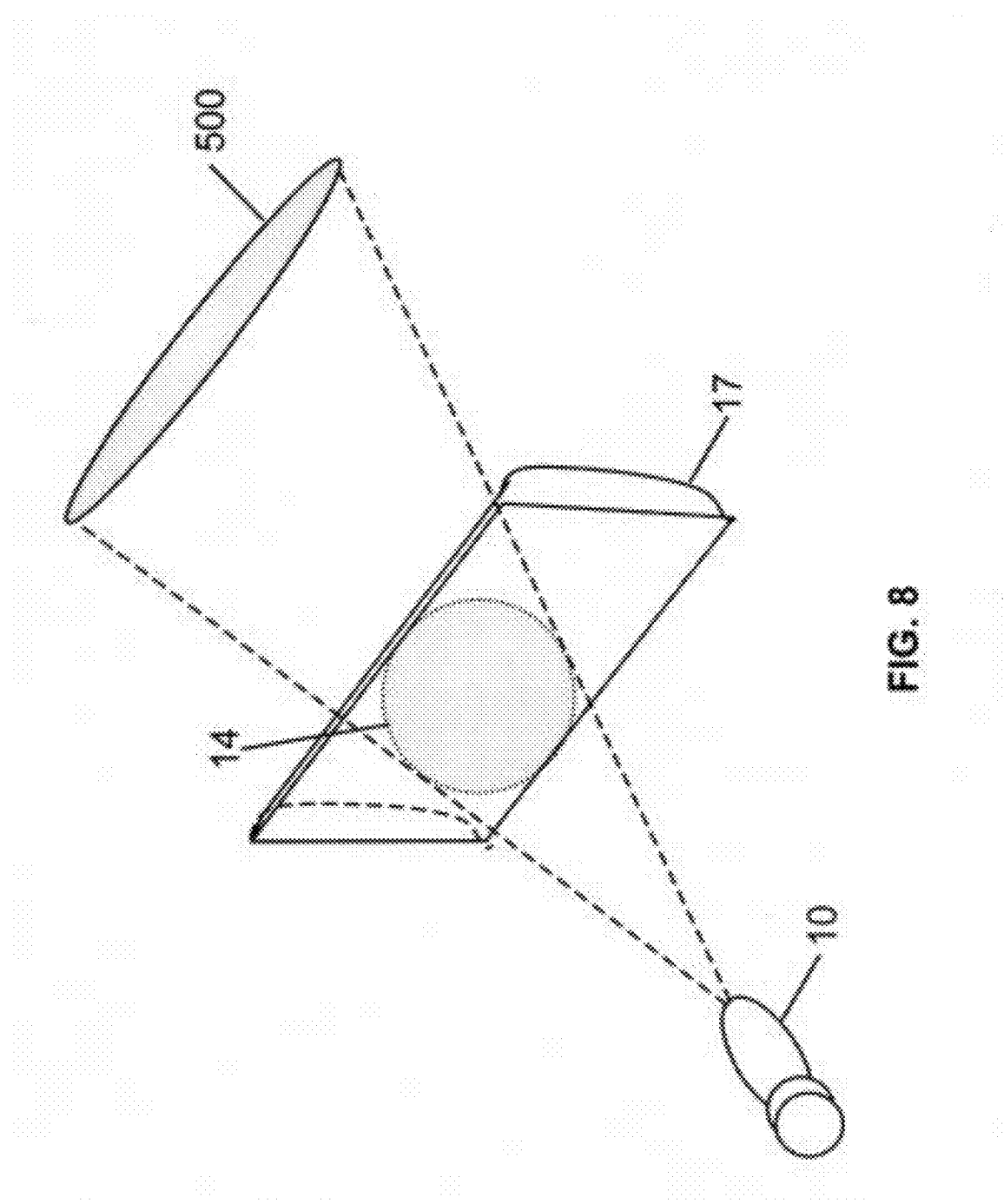

APPARATUS AND METHOD FOR DETECTING THE PRESENCE OF WATER ON A REMOTE SURFACE

Priority is claimed to U.S. Provisional Application No. 61/459,125, filed Dec. 7, 2010, which is herein incorporated by reference.

FIELD OF THE INVENTION

This invention relates to an apparatus and method (and system) for detecting the presence of water (liquid or moisture) on a remote surface, and in particular to an apparatus and method for non-contact optical detection of water on a surface which reduces the effect of ambient light (natural or artificial light) that can negatively impact such optical detection, and also enables installation of the apparatus in non-perpendicular or perpendicular orientations with respect to the remote surface without risk of lowered water detection sensitivity. The invention is useful for detecting leaks and floods in residential environments, in and around commercial properties, or external environments, such as a parking lot, side walk, or staircase. Other substances than water are also detectable upon a remote surface by the present invention, such as oil or alcohol, frozen liquids such as ice, and gases such as water vapor as a mist and heavy gases such as propane.

BACKGROUND OF THE INVENTION

Flood and water damage occurs worldwide to homes and businesses. It typically occurs from leaking pipes, burst water hoses, and plugged drains, but can also be the result of flash floods and storm surges. Timely intervention can minimize the destruction especially to minimize mold and mildew, and cost to repair, which can be considerable. Water damage could be significantly reduced if sensors could be deployed to monitor likely areas for water problems: basements, kitchens, bathrooms. These sensors could sound a local alarm or could be linked to home or business security systems and signals transmitted to a security company or the local fire and police departments.

Known types of sensors are typically direct contact type electrical sensors which monitor changes in capacitance or conductivity as a result of being immersed. Such sensors are placed on the floor and must be covered by several millimeters of water for detection to occur. They can get in the way of foot traffic, can corrode, and may not detect at all if water flows around them without touching them.

An example of the electrical contact sensor is given in U.S. Pat. No. 4,266,195, by G. H. Utke. Likewise, U.S. Pat. No. 7,696,889, titled Fluid Leak Detection System and Associated Method, and U.S. Pat. No. 7,239,246, titled System and Method for Detecting Water Leakage, disclose electrical sensing methods. A device to sense a drop in water pressure when there shouldn't be one is described in U.S. Pat. No. 7,306,008, titled Water Leak Detection and Prevention System and Methods. U.S. Pat. No. 7,562,673, titled Automatic Flow Shut-off System, describes a water heater with a collection pan under it containing a shut off valve. When the valve body gets wet, the paper holding the valve open disintegrates and the valve closes to shut off the water supply. Another device with a similar collection pan is described in U.S. Pat. No. 6,414,598, titled Liquid Leak Detector and Alarm System, where a float in the collection pan rises with a leak and causes the water to shut off. All of the above patents require direct contact with the water or a water pipe.

U.S. Pat. No. 7,224,453 titled Device, Method and System for Determining the Road Surface Condition, describes an optical method in which a frequency modulated spectrometer is directed at the road surface, and the return signal at the frequency of the modulation and twice the frequency of modulation is detected and compared. Such a system, while non-contact, is complex, expensive, and operates differently than the present invention.

There are several pending patent applications that describe water detection systems using electrical sensors, such as U.S. Patent Publication No. 2009/0207031, titled System and Method for Detection of a Variety of Alarm Conditions, and U.S. Patent Publication No. 2007/0024458, titled Water Detection Unit and System. A microphone to sense running water and determine if the water, e.g. toilet, has been running too long, is described in U.S. Patent Publication No. 2009/0224927, titled Running Water Detection and Alert Device for Plumbing Fixtures. It is primarily aimed at toilets whose float valve has stuck.

U.S. Pat. No. 4,690,553 titled Road Surface Condition Detection System, describes a system having a light projector operating in a 1400 to 2500 nm IR range mounted on an arm over a road surface at a different angle with respect to two light sensors. As indicated in FIG. 3 of this patent, such IR range is optimal for detecting a drop in the amount of scatter reflected light from the road surface (i.e., a high signal to noise ratio in the signals from the light sensors), but use of IR range below 1000 nm would negatively affect sensitivity to detect wetness, snow, or ice, since the drop is scatter reflected light and would be difficult to detect. Further, mounting the system of this patent in a home or building, rather than over a road surface, is not practical.

One problem with a non-contact detection system is that ambient light can overload the system, which hinders the detection of reflected light by a light sensor emitted from a source. This problem is especially acute in a non-contact optical detection system using light source operating in the IR range below 1000 nm having a poor signal to noise ratio response when detected. Although light sources, such as light emitting diodes (LEDs) operating in the longer wavelength IR range (1450 nm-1560 nm) are desirable as the source (and also as the detector), since they provide illumination enabling a high signal to noise ratio in the detected signal by a detector sensitive in the same IR range. The problem is that these LEDs in the longer wavelength IR range are expensive as compared to typical low cost LEDs that operate at shorter IR wavelength ranges (940 nm-970 nm). However, use of such low cost LEDs is problematic in that their shorter IR wavelength range is about 100 times less absorbed by water than LEDs in the longer wavelength range, thereby undesirably causing a low signal to noise ratio in the detected signal, severely diminishing sensitivity to water detection, thus making the use of such low cost LEDs heretofore impractical for water detection for example if such were used in the system of U.S. Pat. No. 4,690,553. Thus, it would be desirable if a non-contact water detection system could be made at a lower cost by utilizing lower cost LEDs emitting light at a shorter wavelength IR range, while providing improved sensitivity to detection of water (liquid or moisture), which is further capable of detection of other liquids, or water vapor, ice, mist and other gases, on a surface.

SUMMARY OF THE INVENTION

Accordingly, it is an object of the present invention to provide an apparatus and method for non-contact optical detection of water (e.g., liquid or moisture) on a remote surface with improved ability to reduce or avoid the impact of ambient light, such as direct or reflected natural light source (e.g., sun) or artificial light source (e.g., incandescent or fluorescent lamps).

It is another object of the present invention to provide an apparatus and method for non-contact optical detection of water that can be installed in non-perpendicular orientations, and even perpendicular orientations of its source and detector with respect to the remote surface without risk of lower water detection sensitivity due to specular reflected light from the source.

It is still another object of the present invention to provide an apparatus and method for non-contact optical detection of water on a remote surface using an LED operating in an IR wavelength in the range of 940-970 nm, and in particular 940 nm as an illumination source.

A further object of the present invention is to provide an apparatus and method for non-contact optical detection for not only water (liquid or moisture), but other fluids, or water vapor, mist and other gases, or ice, on a surface.

Another object of the present invention is to provide an apparatus and method for non-contact optical detection of water that has a sleep mode between samples (measurements or readings) to conserve battery power and to sample at intervals that are many minutes apart.

A still further object of the present invention is to provide an apparatus and method for non-contact optical detection of water have a remote device, preferably wireless, having data communication with the apparatus to obtain the status of the apparatus, and send commands to calibrate, or affect parameters of the apparatus operation.

A further object of the present invention is to provide an apparatus and method for non-contact optical detection of water having a digital controller which can utilize averaging of data samples of an analog signal representative of returned light from a remote surface, and adjustable threshold levels for detection of water or other substances on the surface or fault, and thereby improve reliability.

A still further object of the present invention is to provide an apparatus and method for non-contact optical detection of water that provides one or multiple illumination beams which may be tailored or shaped to desired area of detection onto a surface.

It is another object of this invention to provide an apparatus and method for non-contact optical detection of water having a digitally controlled detector which uses synchronous detection and quadrature detection to detect a weak signal in a strong ambient light with a minimum of power consumption.

Another object of this invention is to provide an apparatus and method for non-contact optical detection of water having an alignment LED or laser pointer to aid in the installation and maintenance of the apparatus.

Briefly described, the present invention embodies an apparatus having a source for illuminating a surface, such as the floor of a home or building, with at least one wavelength of light (e.g., in the range of 940 to 970 nm), a detector for receiving returned illumination from the surface sensitive to such wavelength and providing an analog signal representative of the returned illumination, and a controller which samples the analog signal to obtain sample data representative of amplitude of light of the source returned from the surface by the detector. The controller determines the presence of moisture, liquid, ice, vapor or heavy gases, on the surface in accordance with the sample data. The source, detector, and controller are in a housing mountable in a home or building at a distance from the surface (such as 3-14 feet) where water detection is desired. The illumination is projected by the source from the housing along a first direction to illuminate a first region along the surface, and the detector receives return illumination at the housing along a second direction from a second region along the surface. The first region and the second region are the same or substantially overlap along the surface. The detector is operable to provide the analog signal enabling the controller to obtain the sample data for use in determining the presence of moisture, liquid, ice, vapor or heavy gases on the surface when the first direction and the second direction are each perpendicular with respect to the surface and also when the first direction and the second direction are each non-perpendicular with respect to the to the surface. An audible alarm may be provided in the housing which is activatable by the controller such as when the controller determines the presence of moisture, liquid, ice, vapor or heavy gases on the surface.

During measurement mode, the controller determines the presence of moisture, liquid, ice, vapor or heavy gases in accordance with sampled values of the analog signal, preferably by a representative value (e.g., average) of a number of recently stored sample data being below a lower threshold level or value, and the controller determines a fault condition when such representative value is above an upper threshold level or value. The threshold values are set during a calibration mode described below. The fault condition is an indicator that detection of water is being compromised (or prevented), such as by blocking object(s) between the apparatus and the surface the apparatus is to detect water. The fault condition when detected can also result in an alarm which may be audibly different from a water detection alarm. For example, if the apparatus is being used in a warehouse and someone sets a pallet in the field of view of the detector, the reading is likely to go well above the calibration level because the boxes on the pallet are closer than the floor. In such a condition, where the reading exceeds an upper threshold, a warning alarm can be sounded so that someone can visually inspect the area and remove the blocking objects, or perform a recalibration if the blocking object represents a new surface upon which water is to be detected.

In a calibration mode, the lower and upper thresholds are set by the controller in accordance with a calibration level or value by an average of multiple sample values when the first region and second region along the surface is dry. The controller has memory storing a calibration level, upper and lower threshold values, recent sample values, and averages of sample data. The automatically adjustable threshold levels are provided for detection of water, to tune the detection, and thereby improve reliability. The apparatus enters calibration mode at start up, or as desired by a user, such as by pressing a button on housing or an external device capable of sending commands wirelessly to the controller.

The controller controls the operation of the source not only in a calibration and measurement modes, but preferably in a sleep mode. In the measurement mode the source is enabled and measurement and detection of water or fault condition is carried out by the controller, while in sleep mode the source is disabled for a period of time, e.g., at or less than 30 minutes. The controller normally alternates between the measurement mode and sleep modes. The sleep mode avoids the apparatus having to stay on all the time to monitor the floor condition. Continuous operation can run down a battery in the housing in a battery operated residential application of the apparatus. Optionally, power may be supplied externally when the apparatus is mounted such as in a manner typical of a commercial smoke detector installation.

When the controller first detects that the calculated average value is below the lower threshold level (or above the upper threshold level) during measurement mode, the controller enters a rapid detection mode in which the sleep mode interval is automatically reduced by the controller to a rapid detection interval stored in memory (e.g., at or less than 1 minute), thereby increasing the frequency or rate the controller enters the measurement mode after each sleep mode interval. To exit rapid sampling mode, the calculated result (e.g., average of sample data stored in memory) from multiple measurement modes in a row, such as 10-100 (i.e., number of cycling measurement and sleep modes since entering rapid detection mode), must all be in a normal range, i.e., at or between the upper and lower threshold levels. If the average values from multiple measurement modes in a row, such as 10-100, are below the lower threshold level, water has been detected and the water detection alarm is activated by the controller. Such rapid measurement mode may be similarly entered based on the upper threshold to better assure that a fault condition is present prior to the controller activating a fault condition alarm. The rapid sampling mode is used to determine if there is really a problem and react to it, or determine that there was a momentary glitch and after a series of normal readings, go back to sleep mode and then samples on the original preset schedule of measurement and sleep mode intervals.

To improve sensitivity to a reduction in scattered light from the remote surface when water (or other liquids than water, such as oil or alcohol, frozen liquids such as ice, and gases such as water vapor as a mist and heavy gases), the source is driven at an oscillation frequency to modulate the illumination from the source, and each sample (or reading) of the analog signal by the controller is captured at a time in accordance with the oscillation frequency. This minimizes the affect of any ambient light received by the detector in the signal, which can be especially problematic due to direct or reflected natural light source (e.g., sun) or artificial light source (e.g., incandescent or fluorescent lamps) in a home or building along a surface where water is to be detected by the apparatus. In particular, the digital controller uses both synchronous detection and quadrature detection to facilitate the detection of the weak signal (low signal to noise) representative of the returned light in a strong ambient light, especially when the source is a low cost LED operating in the 940 to 970 nm range wavelength. A synchronous detector provides an analog signal representative of the detected light in accordance with the modulation of the source. This analog signal is received and utilized by the controller as described above in measurement and calibration modes. A quadrature detector determines the difference in phase between the oscillator used to modulate the source and the oscillation detected from the signal of the detector. Sampling by the controller is offset by such difference in phase so that samples are captured on or near each peak (+ or −) of the analog signal from the synchronous detector, i.e., when the source illumination output was highest in positive or negative modulated amplitude. The controller preferably determines the sample data for each sample value of the analog signal as the absolute difference of the amplitude of the signal when sampled and the amplitude of the analog signal when previously sampled.

The use of both synchronous detection and quadrature detection reduces or avoids the impact of ambient light, such as direct or reflected natural light source (e.g., sun) or artificial light source (e.g., incandescent or fluorescent lamps) by sampling at the positive and negative modulated amplitude. The quadrature detector makes detection of the analog signal provided by the synchronous detector to the controller immune to phase shifts. These two detection methods operate in combination to allow a low level modulated signal to be detected amidst a much higher ambient light level. Typically, sunlight falling on a floor will be over a thousand times the light level put out by the detection source. The benefit of the quadrature detection is a reduction of the susceptibility to ambient light than can be achieved by the use of synchronous detection alone.

The apparatus may also be used for determining the presence of other liquids than water, or detecting ice, vapor or heavy gases, in accordance with the average sample data being below a lower threshold set for detecting the presence of the substance in the area being monitored by the apparatus.

Preferably, the source comprises an LED providing illumination in an IR range of 940 to 970 nm wavelengths. However, the source less preferably may also be an LED in the longer wavelength IR range of 1450 nm to 1550 nm wavelength. Although contrary to other non-contact water detection systems using IR light to obtain adequate signal to noise ratio in a signal from a detector, in the present invention an LED in this longer wavelength IR range is less preferred since it is more expensive than an LED in the shorter wavelength IR range. An LED in the IR range of 940 to 970 nm wavelengths is also preferably used in the apparatus having more optical power (e.g., 10-500 milliwatts) than that of a typical 1450 nm to 1550 nm LED which only deliver a milliwatt or two. More optical power is available from the source to the surface being monitored and at a lower cost, improving the signal to noise ratio for detecting the reflected illumination of the source from the surface in the detected signal, which coupled with the improvement provided by the use of both synchronous detection and quadrature detection to locate the optimal time to sample the detected signal, provides an improved apparatus for detecting water heretofore not present in the prior art. The detector may also include other types of photodetectors, such as photodiodes or phototransistors sensitive to the source's illumination wavelength.

The source may have optics for directing the illumination from the source to the surface, such as one or more of a parabolic reflector, a lens, or a filter, a prism or a combination thereof. The first region may be of a shape on the surface representing a line (or thin ellipse), oval, ellipse, or circular. When a linear region is desired, the optics may comprise one or more cylinder lenses or prisms for forming a line beam on the surface. The detector may have similar or the same optics as the source for use in the collection of light. The source may provide a cone having a circular cross-sectional shape, or optics may be provided to tailor or shape the beam from the source. For example, a beam having a substantially circular or oval cross-section may be useful for remote surfaces 8 feet or less from the apparatus, while or a narrow or linear (elongated ellipse) beam may be useful for perimeter monitoring, monitoring aisles for spills, or where the remote surface is over 8 feet from the apparatus, in which the more narrow the beam the higher the power density compared to a circular beam. The detector may or may not have similar optics.

The apparatus may have multiple sources of the same or different wavelengths, and one detector, or multiple detectors each sensitive to the same wavelength or to the different wavelengths of the sources. Where multiple wavelength sources are provided in the apparatus, the source-detector combinations for each wavelength are calibrated sequentially using a dry surface and thresholds computed for each source-detector pair. Sample values from multiple detectors may be combined and compared to thresholds described above. For example, the source may represent a plurality of sources of a plurality of different wavelengths, and detector may represent a plurality of detectors at the plurality of wavelengths each providing a different one of the analog signal which is sampled by the controller to provide sample data for each one of the plurality of wavelengths. The controller can then determine a ratio of two values each representative of sample data associated with a different one of the plurality of wavelengths to determine the condition and type of fluid on the surface. Also multiple sources of the same wavelength at different angles with respect to the perpendicular of the remote surface may be provided in the apparatus using a single or multiple detectors. The sampled analog signals from a single detector or multiple detectors may be combined to provide a larger sample value for use by the controller in detecting the presence of water on the remote surface as described above.

Also, preferably the apparatus interfaces wirelessly to a wireless controller to control its operation. This is especially useful when the apparatus is mounted in a hard to reach location, such as when mounted on a high ceiling.

BRIEF DESCRIPTION OF THE DRAWINGS

The foregoing features and advantages of the invention will become more apparent from a reading of the following detailed description in connection with the accompanying drawings in which:

FIG. 1B is another diagrammatic view of the apparatus of FIG. 1A mounted on a ceiling for detecting the presence of water (liquid or moisture) which the direction of illumination by the illumination source and direction of detection of the detector are both perpendicular with respect to a floor;

FIGS. 6A and 6B are top and side views, respectively, of a LED to illustrate how light is emitted there from;

FIG. 8 is a schematic illustration of use of asymmetric beam shaping optics which may be used to shape the illumination from the source of the apparatus of FIGS. 1A and 1B into a linear (or thin elliptical) cross-sectional beam;

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figure 1A:
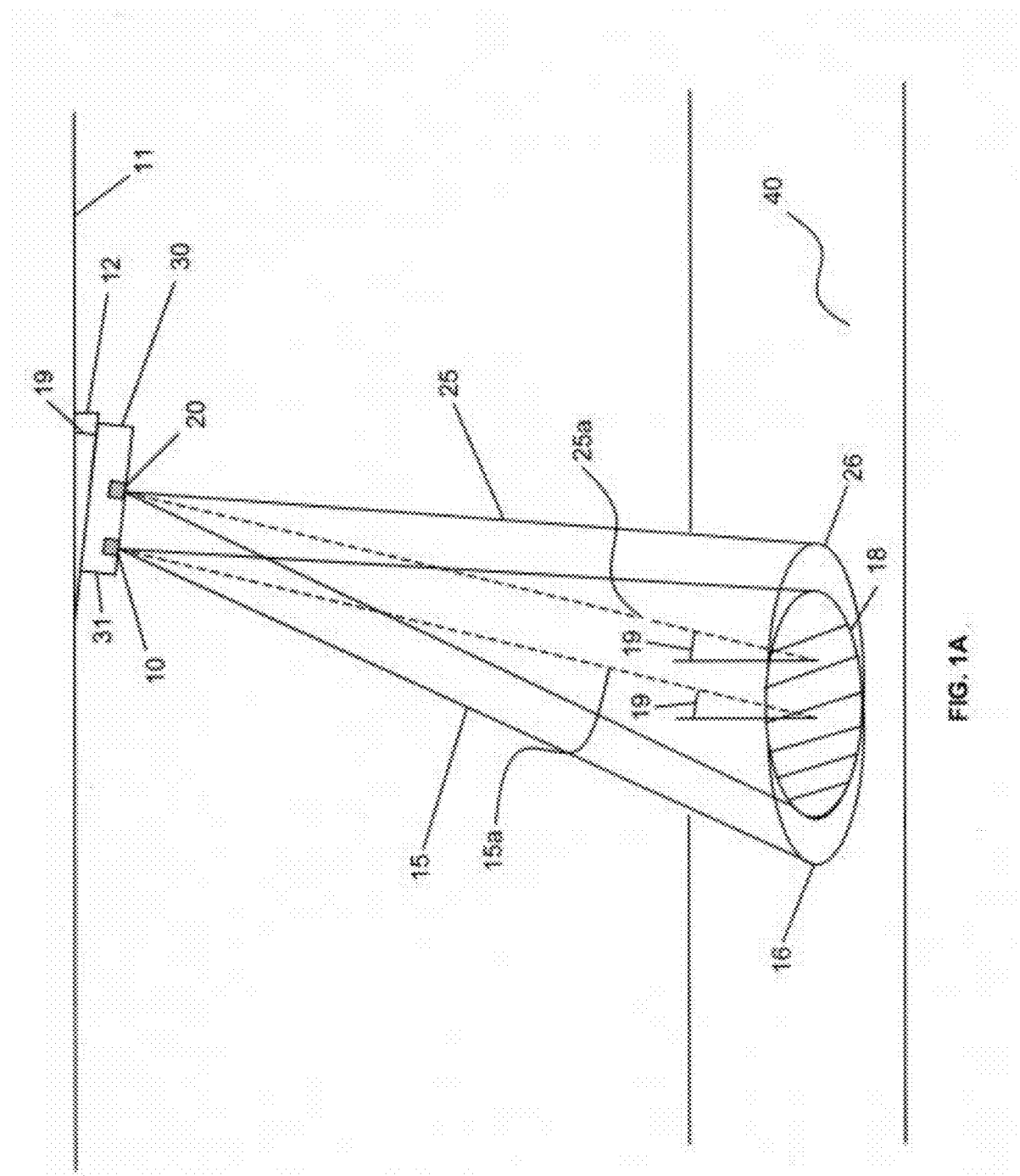
FIG. 1A is a optical diagrammatic view of the apparatus according to the present invention mounted on a ceiling for detecting the presence of water (liquid or moisture) in which the direction of illumination by the illumination source and direction of detection of the detector are both non-perpendicular with respect to a floor.

Referring to FIGS. 1A and 1B, an apparatus 30 of the present invention has a housing 31 mounted on a ceiling or surface 11 having a source 10 with illumination (beam) 15 for illuminating an area or region 16 along a surface 40 and a detector 20 for detecting light with a field of view 25 along an area or region 26 along surface 40. In FIG. 1A, apparatus 30 is mounted to surface 11 using a mounting device 12 to provide a small angle 19 from a normal to surface 40 with respect to the direction 15a of the illumination 15 from source 10 and direction 25a of detection by detector 20 to avoid specular reflections of illumination 15 from the floor or remote surface 40 being received by detector 20. The mounting device 12 may be a bracket enabling mounting of housing 31 by screws into the ceiling 11 at desired angle 19 which may be adjustable by the bracket. For example, angle 19 may be 10 to 20 degrees. In FIG. 1B, apparatus 30 is mounted so that direction 15a of illumination and direction 25a of detection are each perpendicular to surface 40 (i.e., apparatus 30 of FIG. 1A where angle 19 is zero or substantially zero), rather than non-perpendicular as in the case of directions 15a and 25a of FIG. 1A. The mounting to the ceiling 11 in FIG. 1B may be by bracket and screws, such as similar to a smoke detector mounting mechanism.

Source 10 emits electromagnetic radiation, such as of infrared (IR) wavelength, to provide illumination 15 in an extending cone to illuminate a region 16 on the remote surface 40. Detector 20 views a region 26 of the remote surface 40 and collects electromagnetic radiation, such as of infrared (IR) wavelengths, within a detection cone (or field of view). The cross-sectional shape of cones 15 and 25 may be circular or oval. As will be described later in more detail, the source 10 and detector 20 may each have one or more optical elements effecting the shapes of region 16 and 26 and providing a cross-sectional shape different from cone 15 and 25. Regions 16 and 26 are shown slightly offset in FIGS. 1A and 1B, but they should substantially overlap (see cross-hatched area 18) for detection of water (liquid or moisture). If source 10 and detector 20 are identical devices and each utilizes the same optics, their fields of view are the same. To relieve alignment constraints, the detection cone 25 may be larger than the illumination cone 15 to guarantee good overlap in region 18. Having a smaller cone 25 of detection field than the cone 15 of illumination may degrade performance, as will decreased overlap of the source and detection cones. Directions 15a and 25a may be considered the central axis (or dimension) of illumination 15 and detection field of view 25, respectively, or of their respective optics (for e.g., see FIG. 2C).

Unlike the case of non-perpendicular configuration of FIG. 1A, the configuration of FIG. 1B does not avoid or minimize possible specular reflections from the floor or remote surface 40 to detector 20. The signal detection used in apparatus 30, as will be described later below, enables the source illumination and detector detection (15a and 25a, respectively) direction to be perpendicular or non-perpendicular to the remote surface 40, as desired for the particular application, since the water is detectable (when flowing or moving) before a volume of water is established having a smooth reflective surface upon surface 40. In other words, the increased light output by the source and improved signal detection allows for very small decreases in light to be detectable even in high ambient lighting for detection of even small amounts of water before the water becomes a smooth reflecting surface, thereby enabling perpendicular orientation of the source and detector with respect to floor 40 as shown for example in FIG. 1B despite any specular reflected illumination of surface 40 by source 10 being present in the returned light 25 to detector 20. The configuration of FIG. 1B may be particularly useful when surface 40 is of material(s) that diffuses light, such as concrete or carpeting, or in very narrow space applications.

Although the apparatus 30 is shown mounted on the surface 11 of the ceiling for non-contact optical water detection on floor surface 40 in FIGS. 1A and 1B, the apparatus may be mounted on a different surface, such as a wall, floor, or structure, in view of surface 40. Surface 40 may be the floor of a building, although it could be a wall or a ceiling that is being monitored. The distance between the surfaces 11 and 40 depends on the particular environment where water detection is desired, and, as described below, the apparatus 30 is calibrated to provide optimal water detection in accordance with material(s) of surface 40. For example, the distance between surfaces 11 and 40 may be between 3 to 14 feet, and the apparatus may be used in various environments such as a room, basement, attic, or other environment of a commercial or residential building.

Figure 2A:
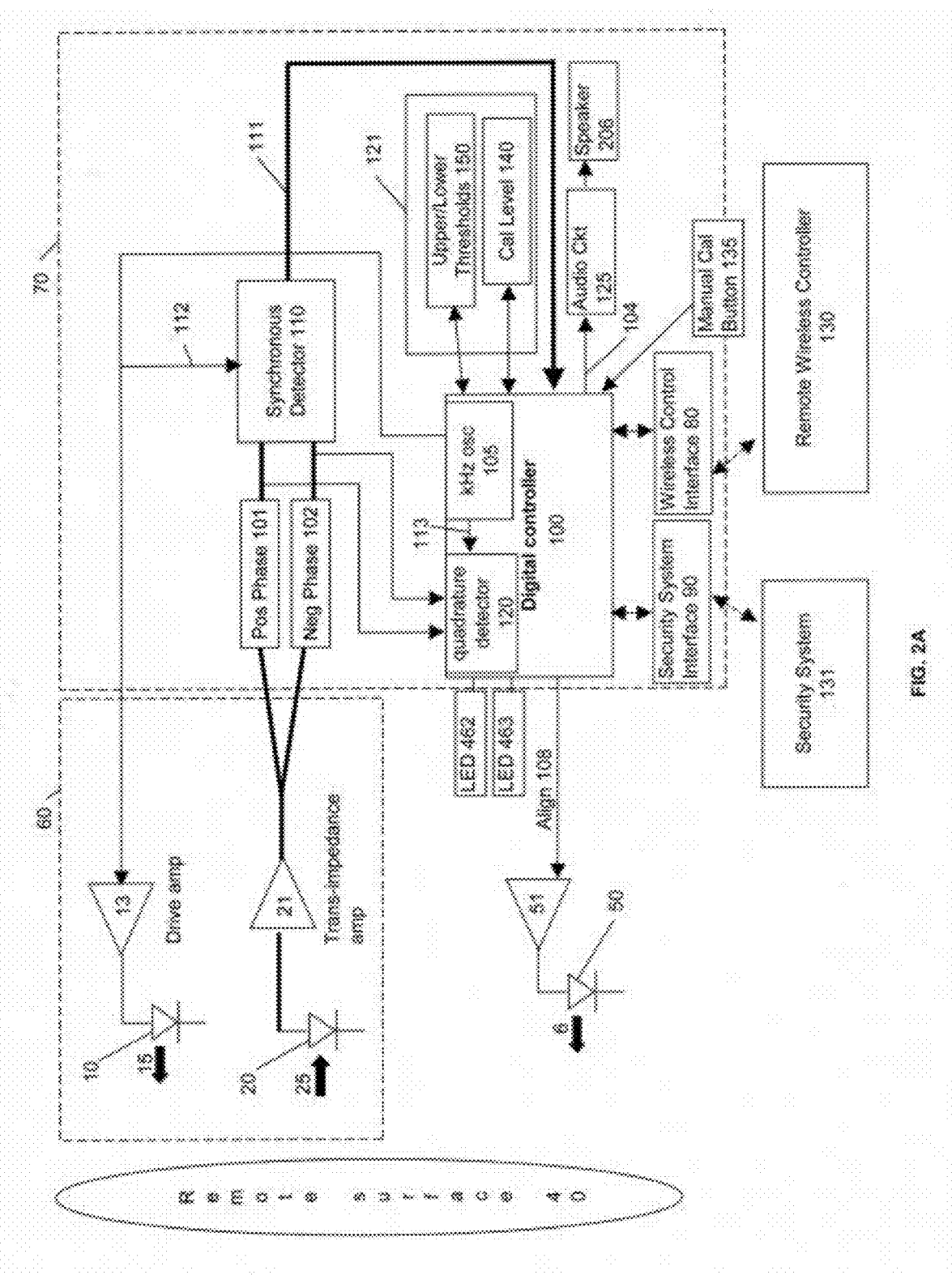
FIG. 2A is a block diagram of the electronics of the apparatus of FIGS. 1A and 1B.

Referring to FIG. 2A, a block diagram of the electronics in the housing 31 of apparatus 30 is shown. A digital controller 100, such as a programmed processor, microprocessor, FPGA, or microcontroller, operates in accordance with instructions (or program/software) in its memory 121 (or external accessible memory) for controlling the operation of the apparatus 30, and enabling calibration mode, measurement mode, rapid detection mode, to enable data communication via an external device, such as wireless controller. For example, digital controller 100 may be an ARM processor, or any one of a large variety of microcontroller options, such as a PIC16F887 manufactured by Microchip Technologies, Inc. of Chandler, Ariz., USA. For purposes of illustration, memory 121 is shown as external of controller 100, but may be external or internal of the chip providing controller 100.

A drive amplifier 13 drives current through source 10, shown for example schematically as an LED, to emit electromagnetic radiation at a wavelength, preferably near IR (e.g., 940 nm), and illuminate the remote surface 40. The source 10 is driven by a signal from an oscillator 105 which modulates the source at a desired frequency, such as 10 kHz. IR light from illumination 15 is reflected (scattered, backscattered, specularly reflected) from the remote surface 40 and some of that reflected light in field of view 25 is collected by detector 20 which has light receiving elements sensitive to the light of the source's wavelength, shown for example as an LED, such as of the same type as source 10. The current generated by the detector 20 is amplified by a trans-impedance amplifier 21 and the resulting signal is split into a positive phase 101 and negative phase 102 signals and sent to the synchronous detector 110, as illustrated by bold arrows of FIG. 2A. The synchronous detector 110 also receives as input the signal from oscillator 105, and processes the positive and negative phase signals to provide an analog signal representative of the detected light by detector 20 in accordance with the oscillation frequency that modulated the source 10. An example of a synchronous detector 110 is a cross-point switch and sample and hold circuit. Controller 100 can enable or disable output providing the signal from oscillator 105 which modulates source 10, via drive amplifier 13. In this manner, controller 100 controls illumination output from source 10, i.e., enables or disables source 10 operation. As will be shown below, source 10 may be periodically disabled by controller 10 when not in a measurement mode or calibration mode such as during a sleep mode to conserve power when apparatus 30 is battery operated.

Although detector 20 is described herein as an element capable of receiving returned light (e.g., photodetector or LED operated as a detector), the detector of apparatus 30 should be considered as not only the illumination receiving element, but also the receiver components enabling an analog signal (e.g., a varying voltage) representative of such returned illumination captured by such light receiving element, such as components (or circuitry) 20, 21, 101, 102 and 110, as well as any optics utilized to improve capture of returned light 25.

Controller 100 samples (i.e., analog to digital conversion) the analog signal from synchronous detector 110 received at the controller's A/D input received, via line 111 from detector 110 when the analog signal corresponds in time to when the source 10 was driven at one of the peaks of its (sinusoidal) modulation. However, sampling the analog signal (which is also approximately sinusoidal) based on the occurrence of such peaks of the oscillator 105 does not provide such optimal sampling, which is due to delay between the time of detection at detector 20 and the time the analog signal from synchronous detector 110 is received by controller's A/D input. In order to solve this problem, apparatus has a quadrature detector 120 which receives positive phase 101 and negative phase 102 signals, and a signal from an oscillator 105, for determining the difference in phase between the oscillation signal (which modulated the source) and that detected by receiver 20. The result is a phase difference (in time), and the digital controller uses this difference as an offset so that the sampling always takes place at or near each expected peak of the analog signal. In other words, the oscillation frequency has alternating peaks of a different sign (+ and −), and quadrature detector 120 enables the digital controller to sample the analog signal at each alternating peak, such that each time a sample is captured the signal corresponds to when the source 10 was driven at one of the peaks. The digital controller 100 stores in its memory 121 (or external memory accessible to the controller) at least every two successive sample readings, where each reading is a value between, for example, 0 and 4095, representative of the amplitude of the analog signal. The sample data is determined by the digital controller 100 by calculating the absolute difference of the current sample reading captured and the previous sample reading captured. As each peak corresponds to a different sign (positive or negative), this is the amount of light 25 returned from surface 40 representative of the light 15 which illuminated the surface 40 from source 10. For example, if the four sample readings are 1000, 2050, 1020, 2100, the sample data are 1050 or |1000-2050|, 1030 or |2050-1020|, 1080 or |1020-2100|. Taking the absolute difference eliminates any constant signal caused by ambient illumination. The quadrature detector 120 and oscillator 105 may be part of the digital controller 100 or separate components there from. The combination of synchronous detector 110 and quadrature detector 120 enables the detection of a weak signal which may be buried in background.

The electronics shown in FIG. 2A has front end electronics 60 and processing electronics 70 which are provided on a printed circuit board in housing 31. Front end electronics 60 comprise the source 10 and detector 20 and their amplifiers, while processing electronics 70 comprises the digital controller 100, and the synchronous detector 110 and quadrature detector 120 which are synched to oscillator 105 such as via lines 112 and 113, respectively. Other electronics include audio circuitry 125, which responsive to a signal 104 from controller 100 the controller can activate (drive) LEDS and a speaker 206 or buzzer. For example, one LED 462 having one or more colors and may be driven at various flash rates/colors indicative of the operating mode of apparatus 30, and another LED 463 may indicate a fault condition detection, water condition detection, or when an input command has been successfully received from wireless controller 130. A calibrate button 135 is provided to send a signal to controller 100 which in response enters calibration mode. A wireless interface 80 is provided enabling controller 100 to send and receive commands to wireless remote 130.

The memory 121 of digital controller 100 or external memory provides storage of all parameters needed for operation of apparatus 30 as described herein, such as registers to hold a calibration level 140 and upper and lower thresholds 150. Also memory 121 stores sample data collected for use determining an average value of sample values for calibration mode and measurement mode. The digital controller 100 preferably averages the sample data to reduce noise. The number of values to average is an adjustable value N from 2-1000, where N is also stored in memory. The digital controller 100 when installed, or reset via button 135 or wireless controller 130, operates in calibration mode in which a dry condition is provided on surface 40, and sample data is averaged and stored in memory as a calibration level 140. Upper and lower thresholds 150 are then calculated by the digital controller 100 and stored in memory. A lower threshold level indicating possible detected water is determined by the controller 100, such as a 10% reduction from the calibration level, and an upper threshold level is determined by the controller 100, such as a 10% increase from the calibration level to determine when a fault has occurred. For instance in the above four sample data example, the calibration level may be 1050, the upper threshold level may be 1155, and the lower threshold of 945. Other percentages may be used based on desired sensitivity. Upper and lower thresholds 150 and calibration level 140 are shown as separate blocks in memory 121 in FIG. 2A for purposes of illustration. Once calibration is completed, apparatus 30 is now ready for water detection.

Optionally, a visible alignment source 50 is provided in apparatus 30, which can be turned on or off by a signal 108 from digital controller 100 to source 50 via amplifier 51. The source 50 is shown as an LED in FIG. 2A, but may be a laser pointer. The beam 16 outputted from source 10, being in the IR range, is not visible. The beam from source alignment guide 50 is aligned with source 10 such that a visible point on surface 40 can be illuminated and identified at the center (or approximate center) of illuminated area 16.

To operate apparatus 30 in the measurement mode, controller 100 enables source 10 (i.e., enabling output from oscillator 105 to amplifier 13 to drive the source), samples the analog signal received from synchronous detector 110, via detector 20, to acquire sample data representing N number of sample values, where each sample value is the an absolute difference of the amplitude of the analog signal when sampled and the amplitude of the analog signal when previously sampled; each of the sample being at times corresponding to two successive alternating peaks, respectively, of oscillator's signal using quadrature detector 120 as described earlier. The previous sampled amplitude of the analog signal is stored in memory 121 so as to enable controller 100 to calculate the absolute difference with the current sampled amplitude of the analog signal. Each of the N sample values are stored as sample data in memory 121 by the controller 100 which then calculates an average value of N sample values, and compares that average value calculated to each of the stored threshold values 150 to determine whether it is below the lower threshold to indicate possible water detection or above the upper threshold to indicate a fault condition. The value N is stored in memory 121, for e.g., N is integer value between 10 and 100, but other values may be used. By using absolute differences calculation of each sample value, an average of multiple sample values, and a tuned threshold value based on desired percentage of sensitivity from a dry calibration value, minimize false water detection alarms which could occur if individual reading were compared to thresholds. For example, if N equals 10, upper threshold level is 1155, and lower threshold is 945, and sample values are 1020, 1010, 982, 940, 944, 980, 1000, 1010, 1005, 1010, then the average value is 990.1, which is between the two threshold levels indicating normal floor condition. If sample values were not averaged and individually compared, the two values just below the lower threshold would have falsely triggered the alarm where overall the N values are on average in the normal range. Accordingly, although individual sample value comparisons to threshold may be used it is less preferable. The average value at the end of each measurement mode (e.g., 990.1) is stored in memory 121 as the apparatus measurement reading with date and time to provide a historical record of operation.

If controller 100 measures over a period of time greater than the time to obtain N number of sample data, then a running average of the last N number of sample data is compared to each of the stored thresholds, and each average value calculated is compared to the thresholds and can be stored in memory. Using the same example above, if the sample values are 1020, 1010, 982, 940, 944, 980, 1000, 1010, 1005, 1010, 1000, the running average value is 990.1, and then 981.1 (average of the last 10 values), and each would be compared to thresholds and at least the last average value determined is stored as the apparatus measurement reading with date and time in the historical record of operation.

The interval of the measurement mode represents the time for the controller to enable the source, capture and compute the N sample values, average such values, and determine possible water detection or fault condition in accordance with such average based upon the N sample values. Optionally, the interval of the measurement mode may be based on a time period stored in memory 121. For example, the interval of the measurement mode may be less than 1 minute. The preferred operation of apparatus 30 will be described in more detail below in connection with FIG. 3.

Figure 2B:
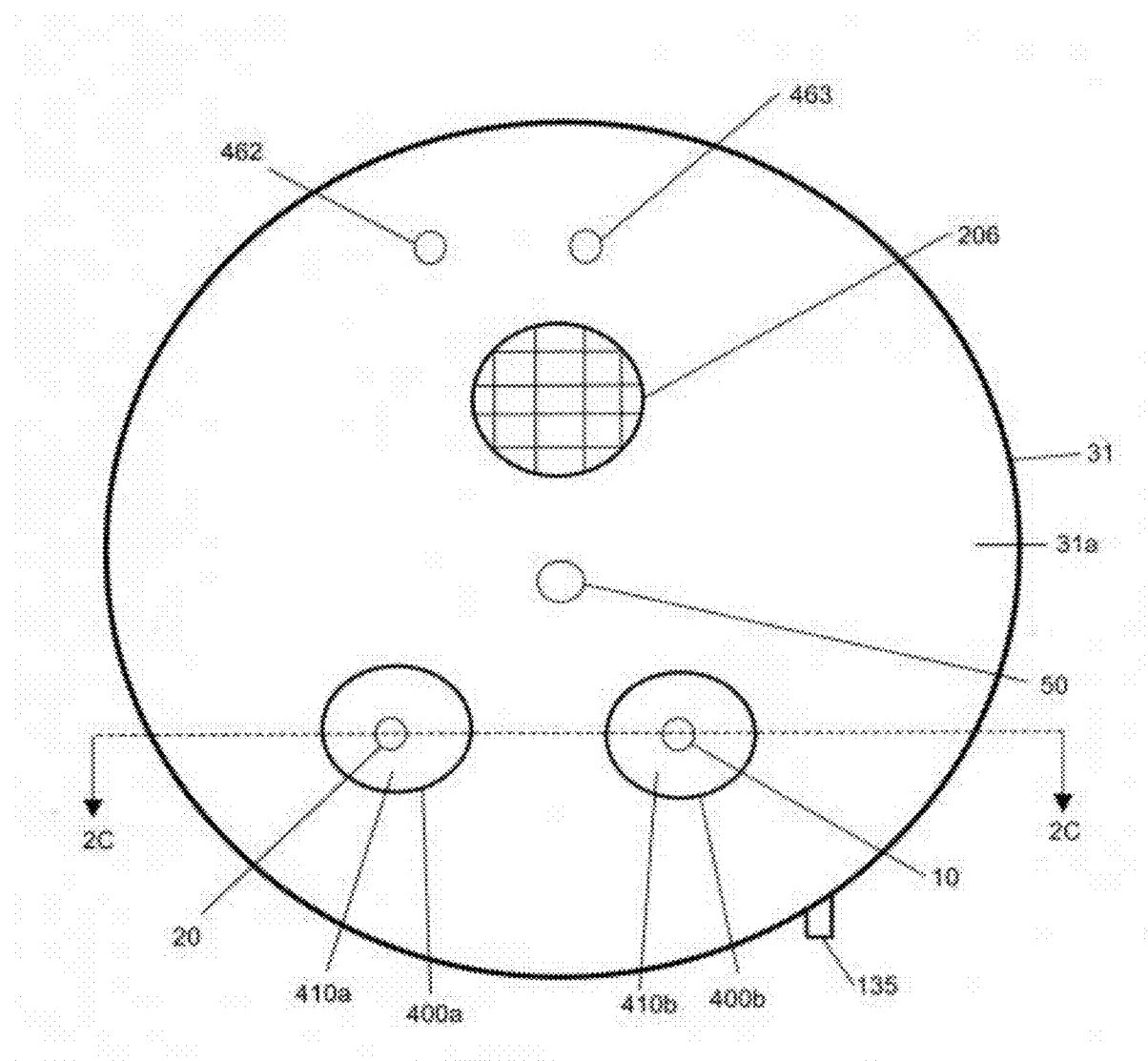
FIG. 2B is a front view of the housing of the apparatus of FIGS. 1A and 1B.
Figure 2C:
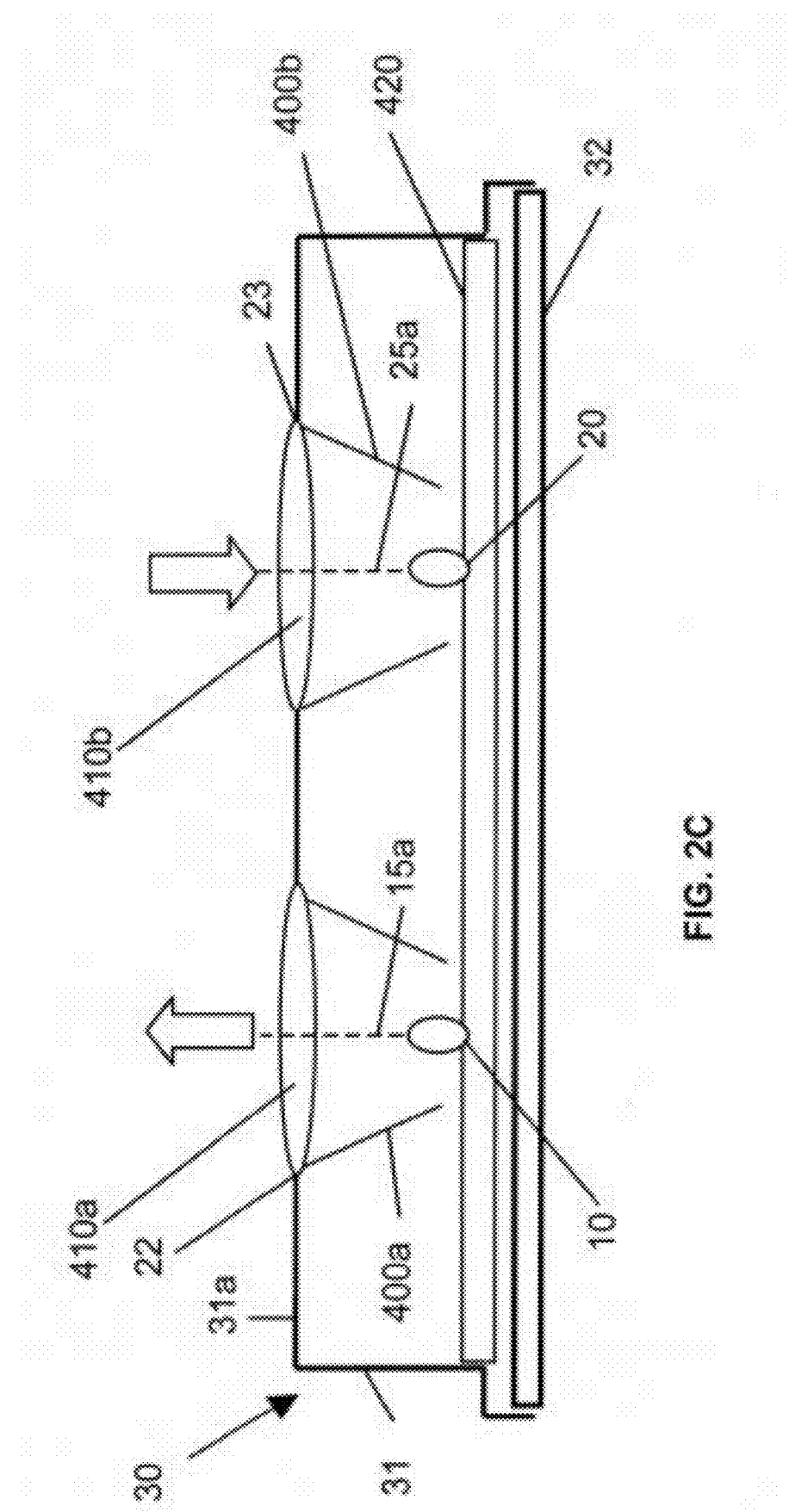
FIG. 2C is a cross-sectional view along lines 2C-2C of FIG. 2B.
Figure 2D:
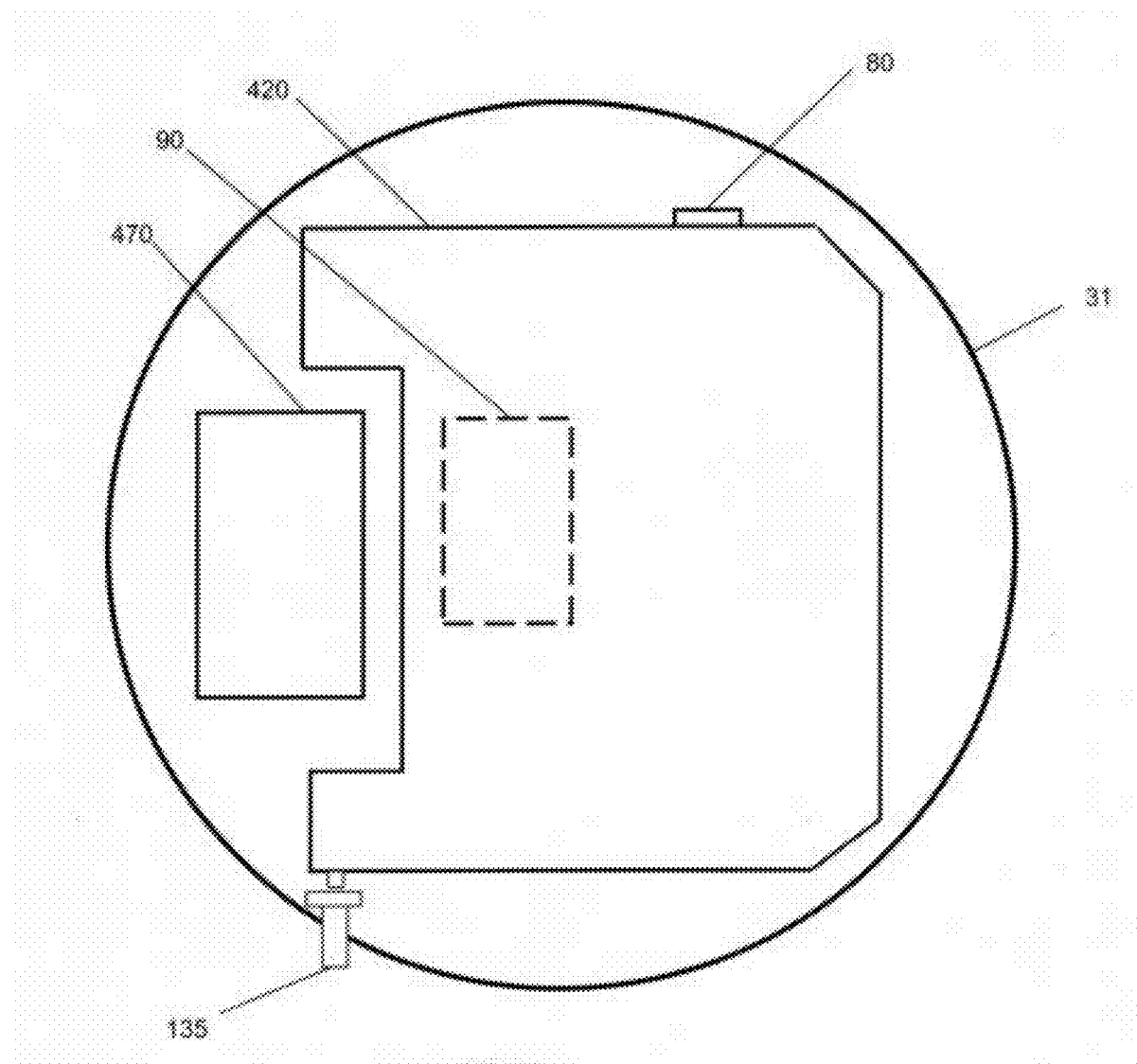
FIG. 2D is a back view of the housing of the apparatus of FIGS. 1A and 1B with back mounting plate removed.

Referring to FIGS. 2B, 2C, and 2D, housing 31 of the apparatus 30 is shown in more detail. FIG. 2B shows the front 31*a* of housing 31, which may be a plastic case or cover 460 releasibly attached to a back plate 32 (FIG. 2C). The back plate 32 is attachable by screws to surface 11 directly (FIG. 1B) or via angled mount 12 (FIG. 1A). As shown in the cross-section of FIG. 2C, source 10 and detector 20 are mounted to circuit board 420 below openings 22 and 23. Reflectors 400*a* and 400*b* surround source 10 and detector 20, respectively. The surface of reflector 400*a* redirects light not emitted towards opening 22 in a direction towards opening 22, such as typical of a parabolic reflector. A lens 410*a* is positioned in opening 22 in front of reflector 400*a* and source 10 to provide the desired beam shaping for illumination 15 towards surface 40. For example lens 410*a* may collimate light into a beam which is circular in cross-section. Another lens 410*b* is positioned in opening 23 in front of reflector 400*b* for collecting light 25 from surface 40 in which collected light not directed towards detector 20 is redirected towards detector 20 by the surface of reflector 400*b*. Lens 410*a* and 410*b* may be the same, and reflector 400*a* and 400*b* may also be the same. Other lenses or optical systems may be used to provide the desired beam shaping and focusing, as needed.

The laser/LED 50 is provided on housing 31 or positioned in an opening along front 31*a*, which when enabled directs light in the same direction 15*a* as illumination 15 to facilitate alignment of housing 31 with respect to the center of a desired region where water is desired to be detected on surface 40, at time of installation of apparatus 30 or to verify the desired region with respect to surface 40. An alarm speaker 206 is mounted in another opening of housing 31. Two LEDs 462 and 463 are on housing 31 or positioned in openings along front 31*a*. LED 462 is activated when apparatus needs calibration, such as on initial install. The calibrate button 135 (e.g., contact switch) is located on the housing such as along the side as shown in FIGS. 2B and 2C, or along front 31*a*, which causes controller 100 to enter calibration mode if pushed. The other electronics described in connection with FIG. 2A may be mounted on circuit board 420, or multiple circuit boards may be used in housing 31.

FIG. 2D shows the rear of housing 31 with the back mounting plate removed, revealing the analog/digital circuit board 420 inside. On the circuit board 420, a wireless interface (or chip) 80 is preferably present for enabling data communication via IR signals with wireless controller 130. Such wireless interface 80 and wireless controller 130 could be instantiated to communicate via RF signals as costs of technologies change. Also visible is the security system interface 90, where the alarms and faults may be reported to a host security system 131.

The apparatus 30 further has a battery 470 which supplies power to the components of the electronics of the apparatus as shown in FIG. 2A. Optionally, the apparatus 30 may be externally powered with or without a battery in case of loss of external power. Circuitry may be present connected to the battery to enable the controller to obtain a data value indicative of the charge on battery 470.

Housing 31 may be similar in size to a typical smoke detector, and having a removable cover to access the battery for replacement, if needed. Housing 31 and its mounting bracket may be made of injection molded plastic. Although housing 31 is shown in FIGS. 2B-2D, other housings may be utilized with the electronic and optical components described herein.

Figure 2E:
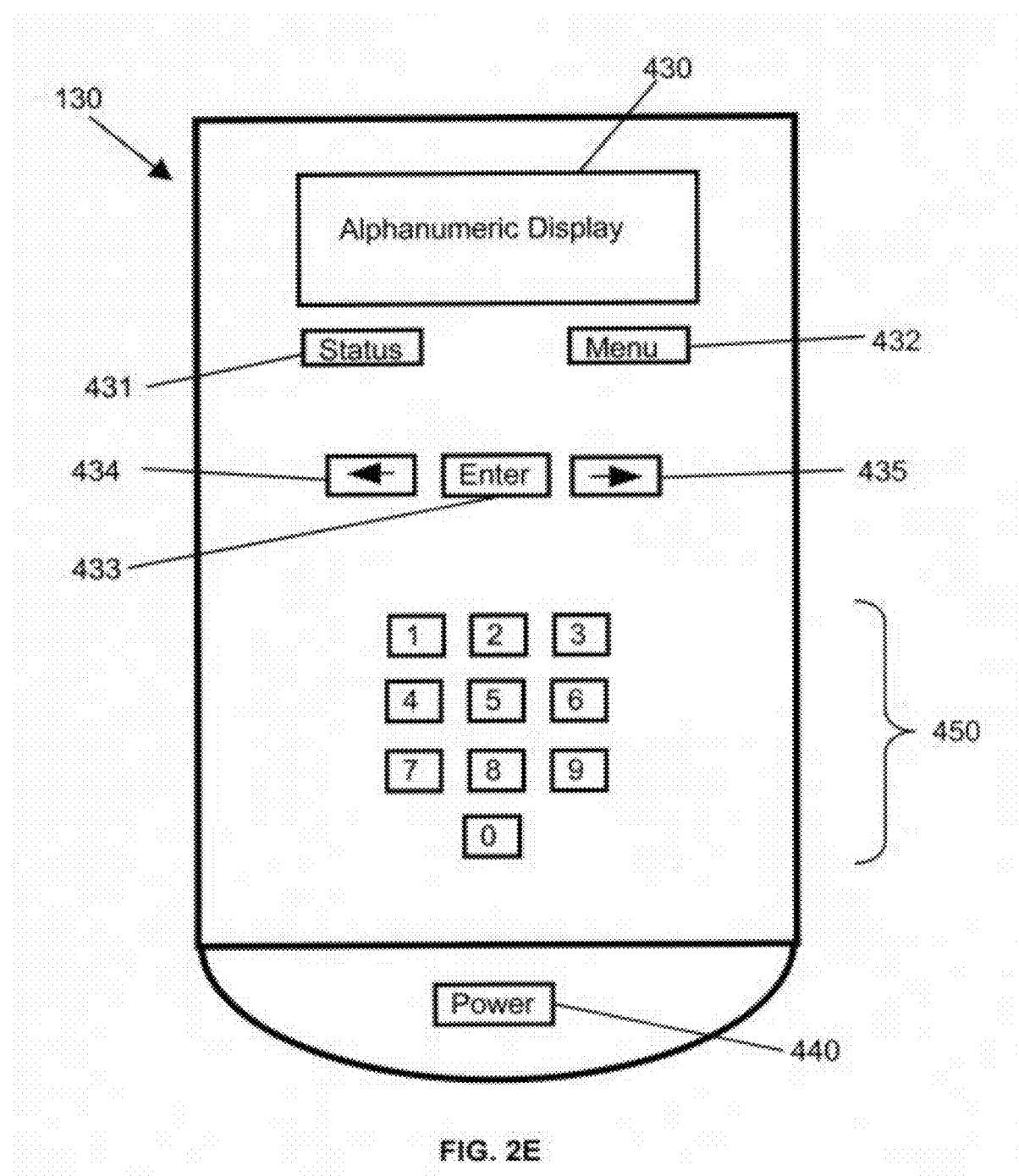
FIG. 2E is an example of the front view of a remote controller for the apparatus of FIGS. 1A and 1B.

Wireless control interface 80 is provided in apparatus 30 through which the digital controller 100 communicates to a remote wireless controller 130, as shown in FIG. 2D. Wireless controller 130 may be similar to a universal TV/VCR/DVD remote, allows transfer of data to and from the apparatus 30, e.g. threshold settings, calibrate commands and monitoring of apparatus status, delivering data back from the apparatus and manual setting of thresholds, if desired. The data can go to the handheld wireless controller and/or to a security system 131 (FIG. 2A) if the apparatus 30 is connected to such a system. The remote wireless device is especially convenient if the apparatus 30 is in a difficult to reach location. An example of wireless controller 130 is shown in FIG. 2E. Electronics, such as a processor or other logic device, operate controller 130 in accordance with software stored in memory of the controller 130, as typical of a universal remote, to enable remote control of a device via IR data communication signals in response to selection of buttons on the housing of controller 130. For example, a power button 440 turns on and off controller 130. A status request button 431 is used to request an update from apparatus 30. A menu button 432 provides options on the alphanumeric display 430, such as an LCD. One can scroll through the menu using the back 434 and forward 435 arrows and pressing enter 433 to select. Thus, the lower threshold can be reset to a numerical value by selecting the reset lower threshold command from the menu, keying in the desired number on the number keys 450, and pressing enter. There is an indicator LED 463 changes color to show that the command has been executed.

Figure 2F:
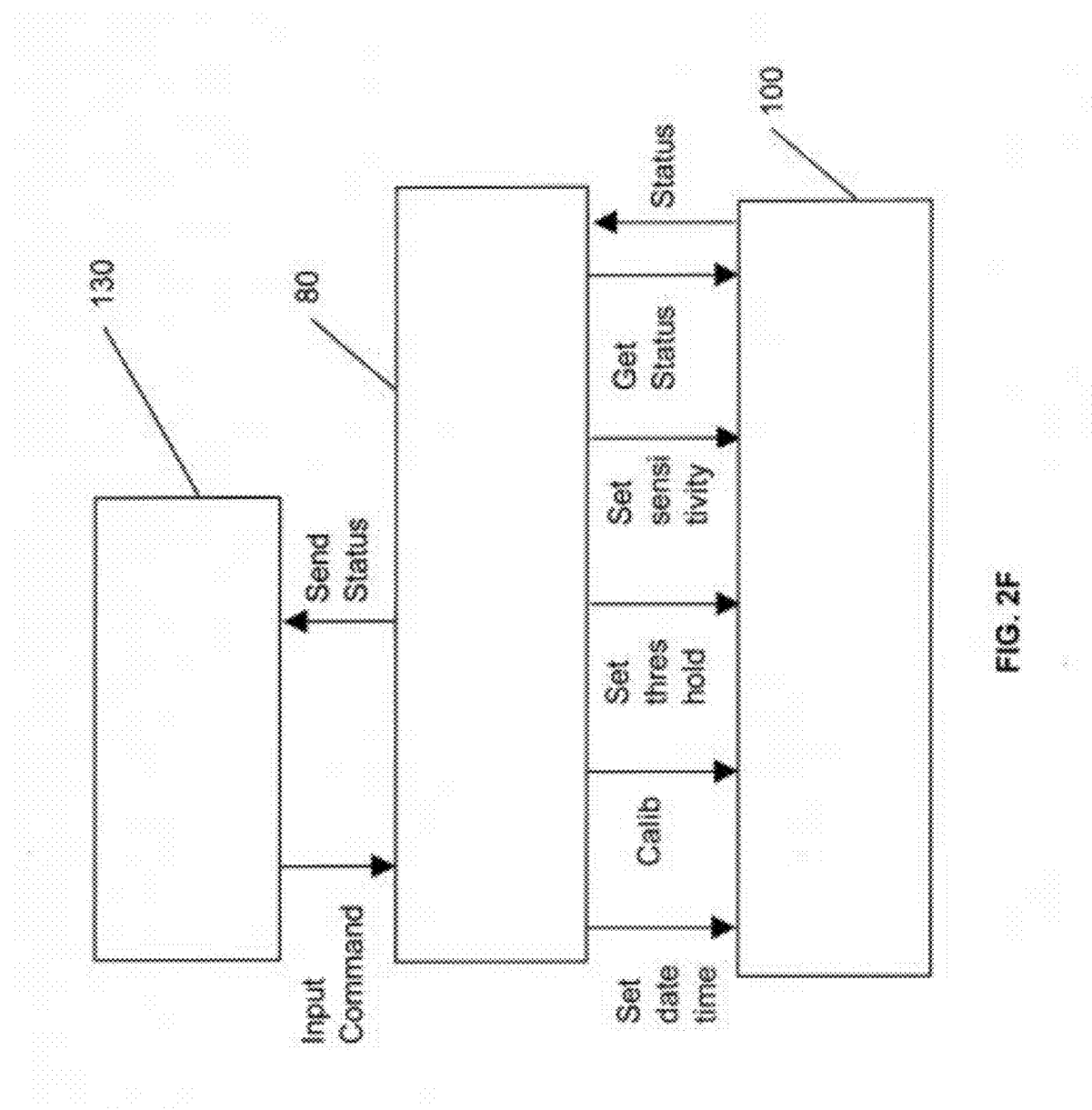
FIG. 2F is a flow chart showing the operation of the remote controller with the controller of the apparatus of FIGS. 1A and 1B.

A flowchart of the operation of controller 110 with wireless controller 130 is shown in FIG. 2F. The wireless controller 130 can send signals to the wireless interface 80 in housing 31 which encode data representative of one of a set of commands and any data associated with such command, which are decoded by the wireless interface 80 for input to controller 100 along one or more lines. These commands are set date and time, set thresholds, request calibration, set the sensitivity level, and get status. The controller 100 operates in response to receiving such commands accordingly, in which in response to set date and time, the controller reset its internal clock accordingly. The controller in response to set threshold, the new threshold levels provided are stored in memory. The controller in response to request calibration, enters calibration mode. The controller in response to set the sensitivity level, sets new calibration thresholds in accordance with a number which may equal or correspond to the percentage used by controller 100 to calculate the threshold levels, as described previously. In other words, the higher the percentage the less sensitivity the apparatus has to detected water and fault conditions. Separate sensitivity levels may be sent for lower and upper thresholds, if desired. When a get status command is received, controller 100 reads memory to obtain the values of calibration level 140, thresholds 150, sensitivity level, sample rate (the rate at which the controller enters measurement mode every hour or day), error flags (flags indicating a fault or alarm was detected), and battery charge, and then sending the data to the wireless interface 80 for encoding as a response message to wireless controller 130 which then decodes and reads the data. As the apparatus may be mounted in an out of reach area, wireless controller 130 enables a user to control apparatus 30 operation. However, any other apparatus 30 operational parameter may be adjustable using wireless controller 130 by inclusion in the command set, as desired, such as output historical record between two selected dates, setting the normal sleep mode interval, and/or in rapid detection mode interval.

Figure 3:
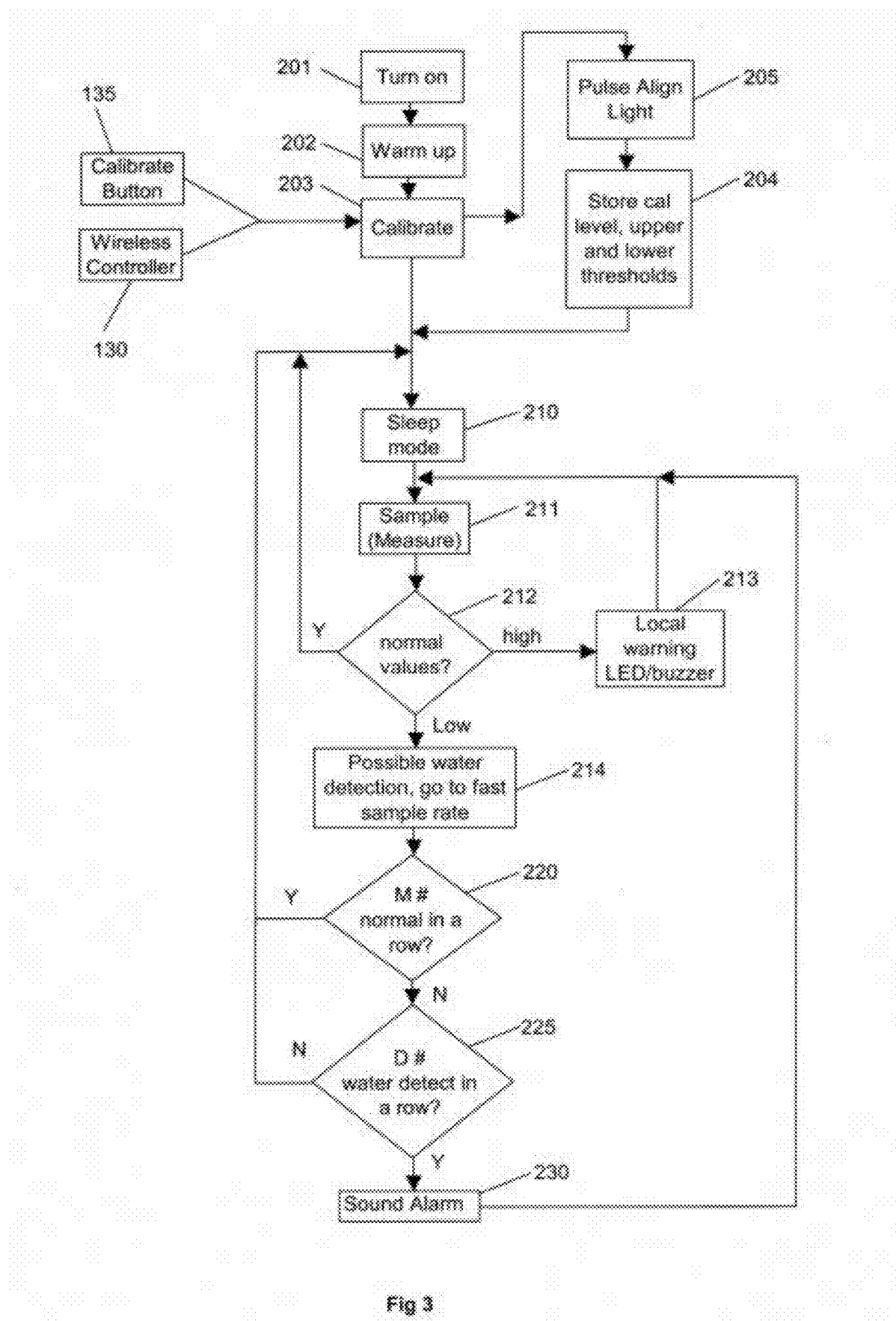
FIG. 3 is a flow chart showing the operation of the apparatus of FIGS. 1A and 1B.

Referring to FIG. 3, a flow chart is shown for the operation of the apparatus 30. First the apparatus 30 is turned on when power is supplied via battery or external power source to controller 100 (step 201), then a warm up period occurs which includes a self test. (step 202). The controller next enters calibration mode (step 203). To operate apparatus 30 in the calibration mode, controller 100 enables the source 10 (i.e., by enabling output from oscillator 105 to amplifier 13) and samples the signal from the detector 20, via synchronous detector 110 in the same manner sample data is determined in measurement mode, over a period of time preset in memory 121, e.g., 1 minute or a preset N number of samples stored in memory 121, when surface 40 in a dry condition. The averages of the data sample is calculated and stored as calibration level 140. The upper and lower thresholds 150 are calculated by controller 100 from the calibration level, as described earlier, and also stored in memory 121 (step 204). At step 205, during calibration mode alignment source 50 is turned on for a brief period (e.g., 2 seconds) by controller 100 for use as an alignment aid, as described earlier. Controller 100 then operates apparatus 30 in sleep mode (step 210) by disabling the source 10 (i.e., disable output of oscillator 105) for a preset period of time, e.g. 30 minutes (i.e., a preset sleep mode interval stored in memory 121), and then in a measurement mode at step 211. Upon entry into measurement mode, controller 100 enables source 10 (i.e., by enabling output of its internal oscillator 105), samples the analog signal from synchronous detector 110 to obtain N number of sample values representative of returned light by detector 20 from the remote surface 40, the N sample values represent sample data which are stored in memory for use by controller 100 to calculate an average value of the sample data acquired during measurement mode operation of step 211.

For example, N may equal a number depending on the desired sensitivity of water detection, but value of N also affects the time duration that the source 10 is on during each measurement mode drawing power from the battery. Thus N is selected which is sufficient to detect water without false alarms (sensitivity) and without causing a large drain on the battery which will undesirably shorten the battery life. For example, N may equal 10, to achieve such balance between sensitivity and battery life, however N may equal 100 if the apparatus 30 is powered from an external power supply, rather than by a battery. With N equal to 10 to 100, the measurement mode interval to obtain N number of sample is less than 1 minute.

If the average value of N number of the sample data stored in memory is at or between the lower and upper thresholds, i.e., a normal value range (step 212), the measurement mode ends and apparatus 30 re-enters sleep mode (step 210). At the end of every measurement mode period, the average value of sample data determined by controller 100 is stored in memory with a time stamp (date and time). If during the measurement mode interval if the average value calculated is above the upper threshold, controller 100 activates speaker 206 to provide a fault condition alarm as well as indicating such on LED 463 as a color or rate change (step 213). If the average value calculated is below the lower threshold, then the sleep mode interval is automatically shortened, e.g., 1 minute, by controller 100 and apparatus 30 enters a rapid detection mode, as such is an indication of possible a water or liquid leak (or moisture) on surface 40 (step 214). At this faster rate of alternating sleep and measurement modes repeating through steps 210-225 until the average value stored for each of M number of measurement mode periods in a row are in the normal value range (step 220), such that apparatus 30 exits rapid detection mode by resetting the sleep mode back to its previous sleep mode interval stored in memory 121 since possible water detection on surface 40 could not be verified. However, if the average value stored for each of D number of measurement mode periods in a row are below the lower threshold, the controller (step 225) has determined (and verified) the presence of water (or moisture) or a leak condition on surface 40 and triggers a water detection alarm by controller 100 activating speaker 206 as well as indicating such on LED 463 with a color or rate change (step 230) thereby providing notification enabling corrective action to be taken to prevent further water on surface 40. In addition to such local alarm at step 230, a remote alarm signal may also be provided to a residential or commercial security system 131 (FIG. 2A) in a home or building via a security system interface 90 enabling data communication between security system 131 and controller 100, so as to send an alarm message to the security monitoring contractor. Such interface 90 to security system 131 is optional. For example, M and D may be set to 10, or D may be set to a different value from M, such as 5. The audible signal of speaker 206 indicative of a water detected alarm at step 230 may be different (e.g., tone, buzzer, or beep rate) from that indicative of a fault condition when an upper threshold error is detected at step 213 in accordance with signal 104 sent to speaker 206 via audio circuit 125.

Alternatively, the process of FIG. 3 has no sleep mode and the system continuously operates in measurement mode, unless in calibration mode. Steps 220 and 230 are provided to rule out false alarms, however such may be omitted and after step 214, water detection alarm may be activated by controller 100. The various intervals of sleep and measurement modes, M and D, are presented as examples and can be adjusted in software used by the controller 100 and stored in memory, to provide the desired sensitivity. Also, after calibration is completed at step 203, the calibration level and thresholds can be automatically sent to the wireless remote 130, if desired, for display if the wireless controller is on.

The wireless interface 130 can interrupt the process flow of steps 210-225 at any point by sending in a command, or requesting status and data as described earlier via wireless interface 80. On command completion, normal process flow of steps 210 to 225 resumes. Also calibration at step 203 may be initiated by pressing calibration button 135 on housing 31 or via wireless controller 130, as indicated in FIG. 3.

Thus in operation, the source 10 illuminates remote surface 40 and a detector 20 detects returned light reflected from this remote surface 40. A signal level for a dry condition is established as a calibration level 140 for a given surface and installation geometry, by using an average of multiple samples. An upper and lower thresholds 150 about the calibration level are established. If the presently detected level falls below the lower threshold, it indicates the presence of a liquid or undesirable substance in the field of view of the detector 20. If the presently detected level falls above the level of the upper threshold, a warning of fault is given to investigate the condition of what is blocking the apparatus from properly operating. Such detected water warning and fault warning may be provided by audio circuitry (speaker) and/or visual circuitry (LED) via signal(s) from digital controller 100 or through interface to security system 90. Most likely, a fault condition is when someone has placed a box, pallet, or other object in the field of view of the detector, and being closer to the detector, gives a higher signal. Such a situation needs to be rectified to enable water detection on surface 40. If the blocking object now represents the surface 40, the apparatus needs to enter calibration mode such as by manually pressing button 135 on housing 31 or via wireless controller 130 calibrate command to controller 100.

Figure 4A:
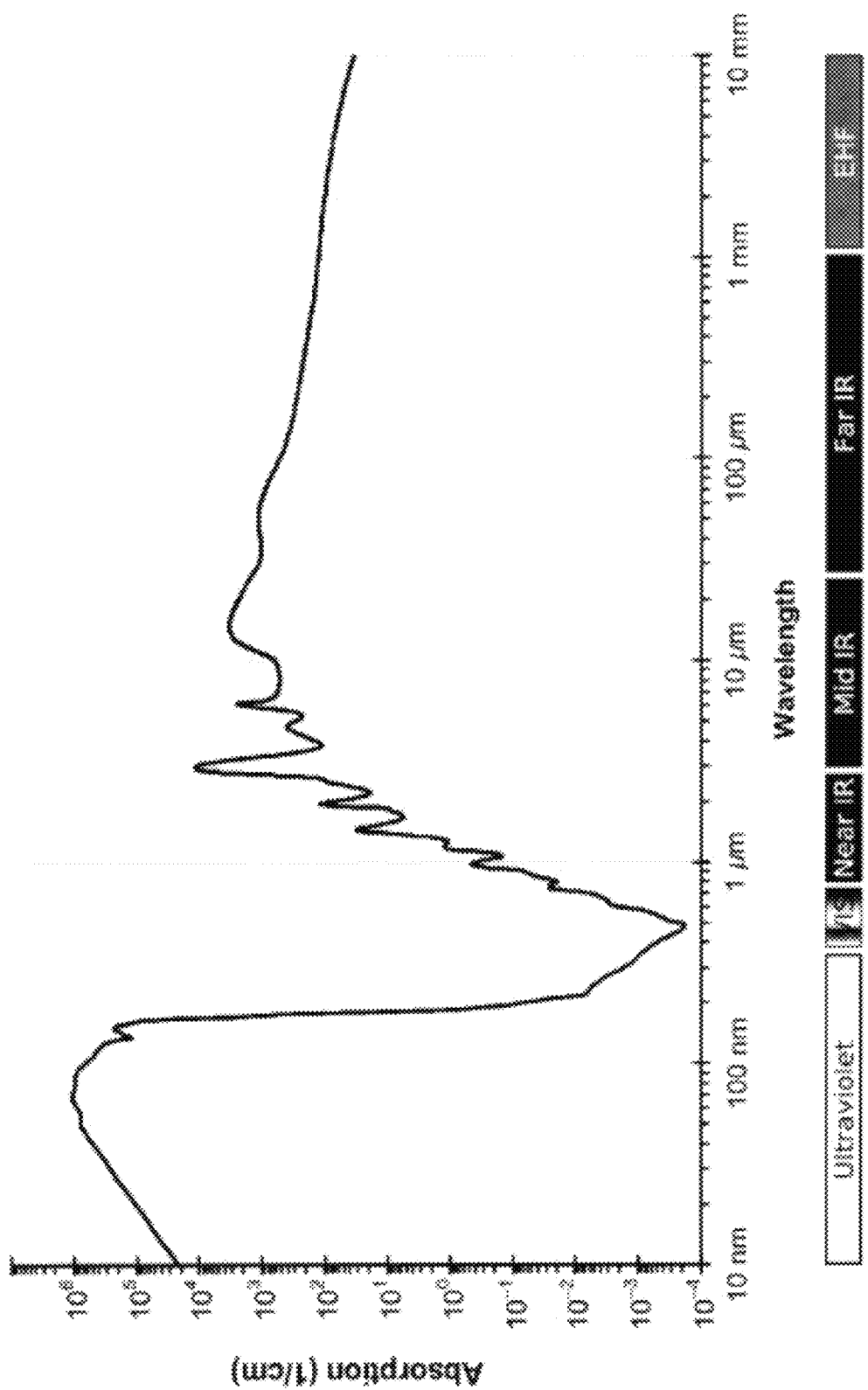
FIG. 4A is a graph showing the absorption of water versus wavelength.
Figure 4B:
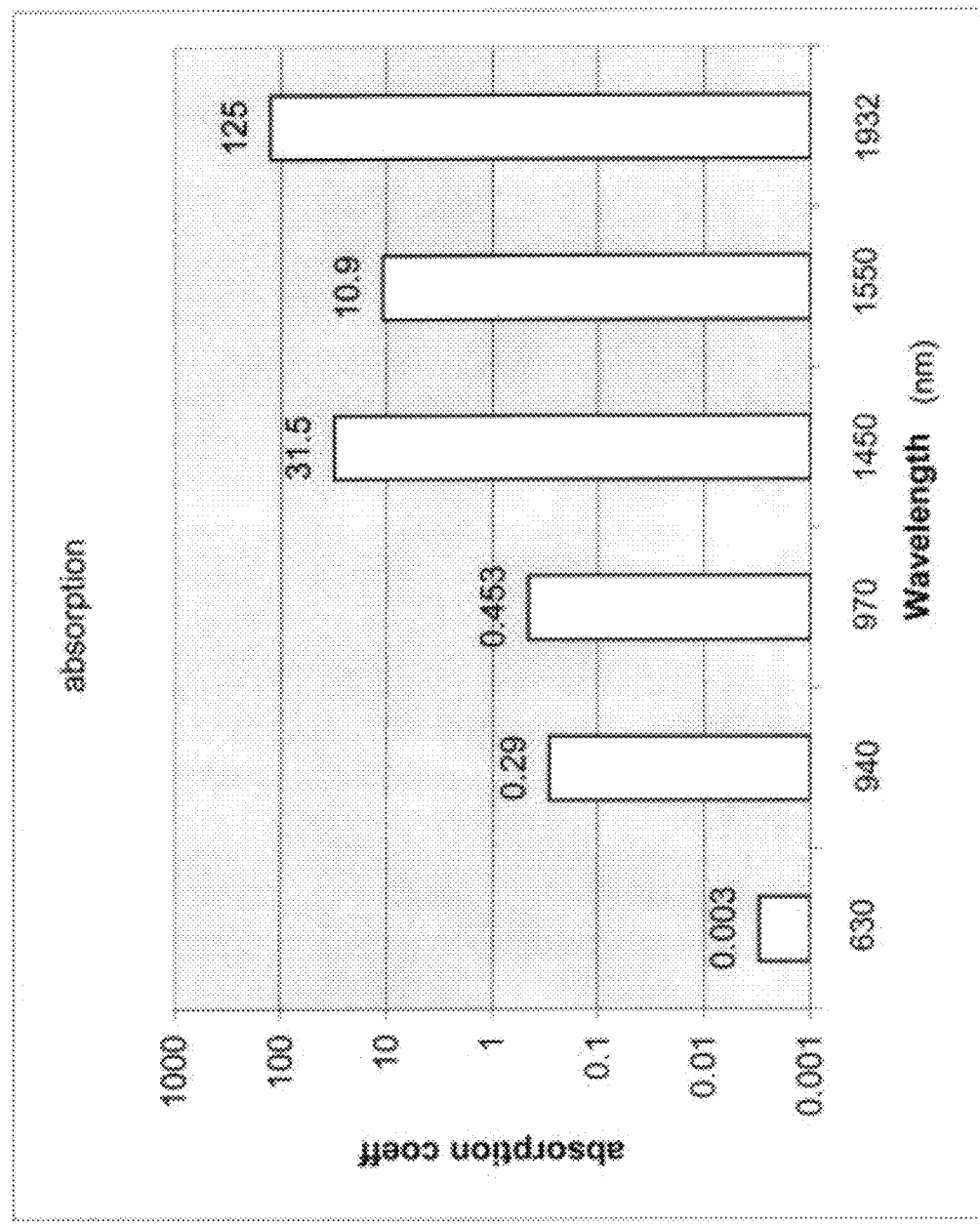
FIG. 4B is a chart showing the absorption coefficients of water in the near infrared.

FIG. 4A shows the absorption of light by water at the visible and near IR, while FIG. 4b shows a chart of absorption coefficients for water for various wavelengths. Absorption peaks occur at 970 nm, 1450 nm, and 1932 nm. LEDs are commercially available at 940 nm, 1450 nm, and 1550 nm. The absorption peak at 1932 nm is the highest in the near IR, but economically viable sources and detectors are not yet available. The absorption at 940 nm is about 100× less than at 1450 nm. Absorption spectra for other liquids can be obtained to find optimum wavelength choices for those. Two sources of different wavelengths can be used and the ratio of the signals at the two wavelengths can be used to determine which liquid has leaked, for example, fuel oil or water. More than 2 wavelengths can also be used.

According to FIG. 4B, the second best wavelength for water should be 1450 nm where the absorption is the highest. At 1550 nm, the absorption is about 3× lower, and about 100× lower at 940 nm. Conventional wisdom dictates that 940 nm is a poor choice, since the signal to noise ratio of the analog signal sampled by the controller 100 is poor as compared to 1450 nm or 1550 nm. However, LEDs at 940 nm are abundant, inexpensive and can be purchased with many times the power of a 1450 nm or 1550 nm LED which only deliver a milliwatt or two. Further, it is cheaper and easier to use a 940 nm source to handle the long distances of high ceiling warehouses (20 to 30 feet) than to use a plurality of 1550 nm devices and maybe a plurality of detectors also. LED detectors provide very little current, around 50 picoamps. They are not very good at collecting light because much of the surface is covered with an electrode. Furthermore, putting a lens in front of the detector only increases the signal by about 1.5× where a 100× increase would be expected based on the lens diameter to LED diameter. At 1932 nm to about 1400 nm, phototransistors are not commercially available at this time but would be a good choice for a detector when available. Shifting to 940 nm allows the use of a silicon phototransistor with a peak response tuned to 940 nm and an internal gain, delivering a current of a few milliamps, a billion times that of an LED. Furthermore, phototransistors are made to receive light and using a collector lens in front of the phototransistor can give close to the calculated 100× boost in signal. For increased range (20-30 feet) and increased cost for commercial devices, silicon avalanche photodetectors can be used and photomultipliers, especially those with extended S-1 photocathodes can be employed for extra gain. The use of an S-1 photocathode or extended S-1 photocathode, means that image intensifiers (beam finders) can be used. Now one can actually see the beam one is working with, making testing and installation alignment much easier. Farther out in the infrared, at 1450 and 1550 nm, only very expensive video cameras can detect the beam. Although there is a 100:1 hit in absorption by moving to 940 nm, there are many offsetting advantages to a shift to 940 or 970 nm. Liquids, especially water, can be detected readily with 940 nm illumination. The percent drop is lower than at 1450 nm for many substances, but the overall signal level is much greater because of increased light and a noise immune lower threshold can be set. In short, 940 nm not only works but it can work better than 1450 and 1550 nm, a very counterintuitive result.

IR lasers, although feasible, are not as good a choice as LEDs because of restrictive CDRH regulations on IR devices because there is no blink response or aversion reflex. A tungsten lamp with a filter and chopper wheel is another alternative for a light source for synchronous detection. It is also known to use microwave or millimeter wave signals to detect water, e.g., Doppler weather radar, but such techniques are beyond the economic scope of this invention. Likewise, visible and UV wavelengths can be used to detect water or other liquids, but the UV LEDs are not very economical and the visible are not very practical at this point in time. It could be annoying to have a visible light shining on the floor of a store or a hallway. Ultrasound does not travel through the air without serious attenuation.

Figure 5:
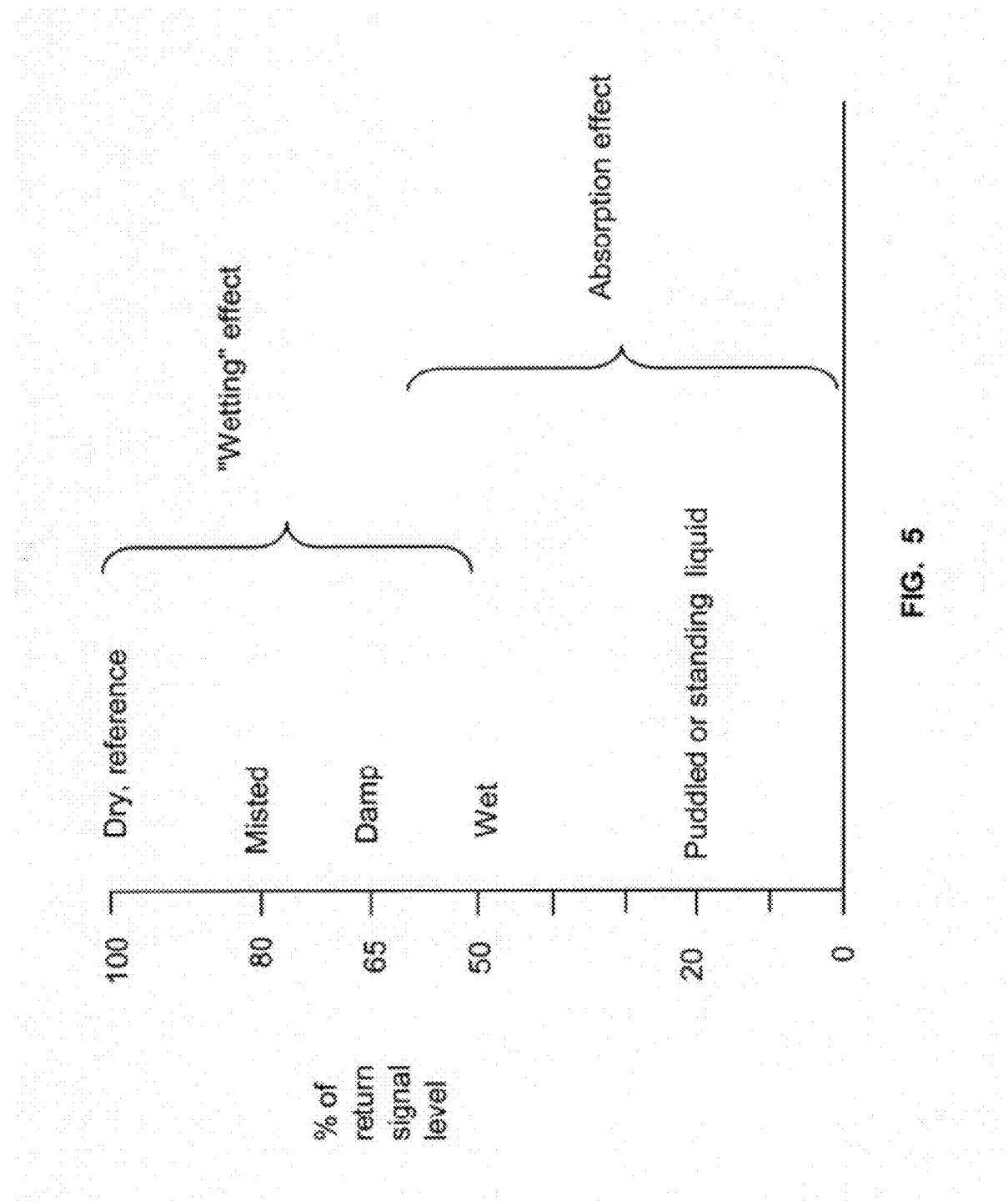
FIG. 5 is a chart showing how signal drop is related to "wetting" of a surface and absorption.

FIG. 5 shows some of the reasons why LEDs selected for water work on other liquids and why shorter, lower absorption wavelengths also work. Surfaces can be classed as hydrophilic (attracting water—"wettable") or hydrophobic (repelling water—"non-wettable"). Several processes occur when liquid is spilled on a wettable surface like a towel or bare concrete. The surface darkens due to light trapping such that light is forward scattered deep into the cloth or surface. Also, the water or liquid layer reduces the delta index of refraction, decreasing the reflection off the material, similar to an anti-reflection coating. In addition, there is the pure absorption of light by the liquid. Once a sheet of liquid covers the surface, whatever Lambertian (diffuse) surface to reflect light in all directions is gone and the liquid acts as a specular reflector. For this reason, one has to be careful to minimize such reflections back to the apparatus 30 because the signal level may rise above the calibration level and the apparatus 30 will determine there is no liquid when, in fact, there is a lot of liquid. A tilt of a few degrees with respect to the normal of the remote surface will eliminate this problem. Hydrophobic surfaces do not "wet", and the water beads up on the surface. Only a millimeter or less is needed for a significant drop in signal and beads of water can easily be 2 mm high even on vertical surfaces, thus triggering a liquid leak alarm. Ice can likewise be detected because the frosty surface and internal bubbles tend to scatter light and return less light than ordinary water. Similarly, water vapor mist decreases the signal by forward scattering and absorption. A heavy gas, like propane, works strictly on absorption. In FIG. 5, the dry surface represents 100% of the returned light, once a calibration is made. A calibration measures the signal coming back from a reference dry surface. It automatically compensates for the darkness of the surface, the color, the Lambertian (rough, diffuse) or specular (smooth, shiny) nature of the surface and the distance from the apparatus 30. The surface can then be misted with the liquid from a spray bottle. A definite drop in signal, 20% as shown in the figure, can be detected with just a couple of sprays. More sprays make it damp and the signal level drop may be 30% down from dry. Getting the surface wet, without standing water may take the signal down to half of dry. When puddles or standing liquid form, then the signal can drop more than 90% from the dry level. In this region, pure absorption is involved. The point is that a substantial drop in signal level occurs without pure absorption being the factor. Put another way, the first half of the signal drop is non-specific detection of liquid (could be water or oil, or alcohol), and the second half can be very specific (definitely fuel oil). In this way, different wavelength sources can be used and the ratio of signals employed to determine the exact liquid, should that be necessary. Most of the time, the fact that a leak has occurred and needs to be corrected is all the information that needs to be conveyed. It doesn't matter what the liquid is, it shouldn't be there. Non-wettable surfaces rely solely on pure absorption. The percent signal drop is much lower than for wettable surfaces for small amounts of water, but catches up when the surface is flooded. Typically, a 1 to 2 millimeter layer of standing water will cause a 90% drop in signal from the dry level.

The apparatus 30 can also be used to detect certain substances in gaseous form. One such substance is water vapor as a mist, as from a shower or a boiling pot of water. Strictly speaking, such a "cloud" of water vapor is not a gas but a colloidal suspension of tiny droplets in air. Some actual gases, such as propane can be detected because they are heavier than air and collect in a thin layer near the floor.

Figure 6A:
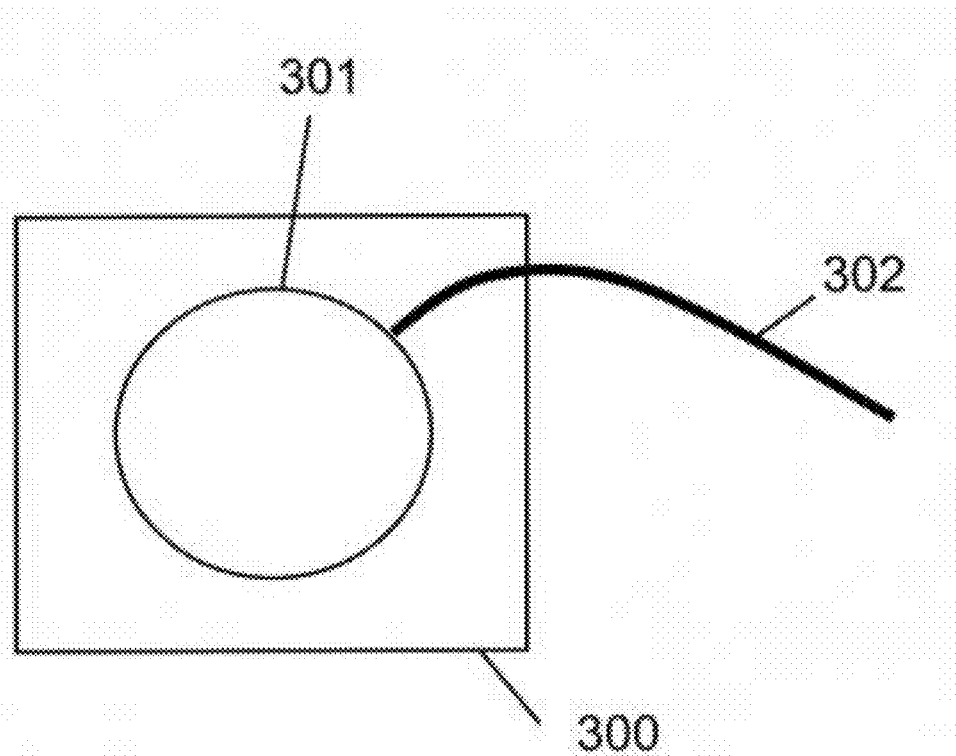
Figure 6B:
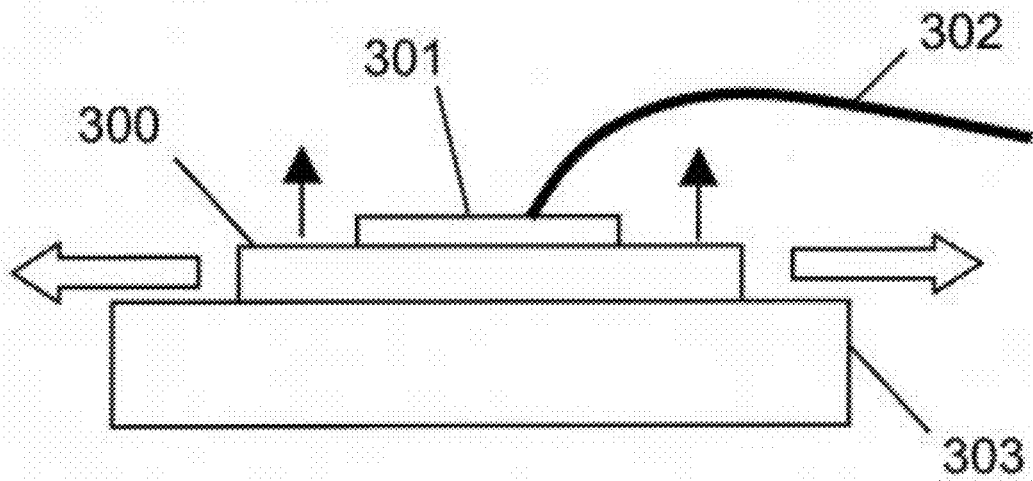
Figure 7A:
FIGS. 7A and 7B are optical diagrams showing an example of various optics that may be use with the illumination source of the apparatus of FIGS. 1A and 1B.
Figure 7B:
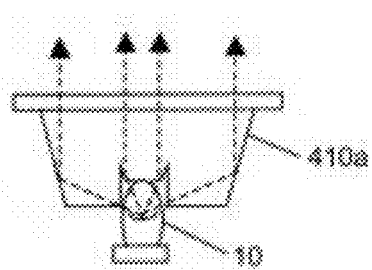
Figure 7C:
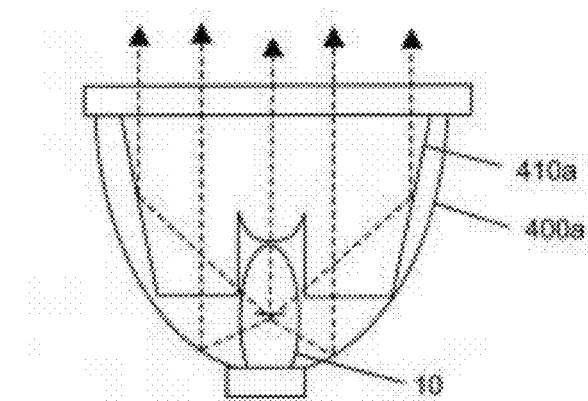
FIGS. 7C and 7D are optical diagrams showing the optics for use with the illumination source and illumination detector, respectively, of the apparatus of FIGS. 1A and 1B.
Figure 7D:
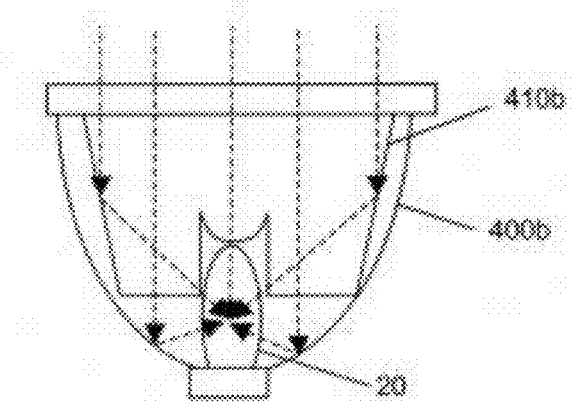

Referring to FIGS. 6A and 6B, a top view and a side views, respectively, of a typical LED is shown. LEDs were originally designed as indicator lights and wide angles of emission were actually good. As the top view shows, the LED chip 300 has an electrode 301 on the top surface which blocks most of the light from coming out the top. A wire 302 makes contact with the electrode. The LED chip 300 is mounted to a substrate 303. None of the light emitted on the optical axis escapes, being blocked by the electrode. The side view shows that much of the light escapes out the side. Accordingly, a parabolic reflector 400 may be positioned around the LED providing source 10 to direct this side light to the remote surface 40 and focus the light onto the surface 40 by moving the reflector 400 with respect to the LED along the optical axis. Parabolic reflector 400a is shown for example in FIG. 7A. In addition to the reflector, a collimator lens 410a may be used to uniformize and reduce the angle of the emitted beam, FIG. 7B as shown by the arrows indicating outgoing light from the source. FIG. 7C shows the combination of a reflector 400a and a collimator lens 410a on the source 10. Likewise, the same optics can be placed over the detector 20 to work in reverse to improve light collection as shown in FIG. 7D. Other optics which may be used with source 10 and detector 20 may include filters to reduce ambient light and cylindrical lenses or prisms to form asymmetrical beams. Beam shaping can be to any desired format. For example, FIG. 8 shows how an elliptical or "line" beam is generated using a cylinder lens. The LED source 10 forms a circular expanding beam 14. A cylinder lens 17 focuses the beam in one axis forming a "line" or narrow ellipse beam 500 on the surface 40. A prism(s) or grating(s) can similarly be used. Other beam shaping may also be used as desired to obtain the desired coverage on a remote surface. Different uses of elliptical beams 500 are shown in FIGS. 9 and 10.

Figure 9:
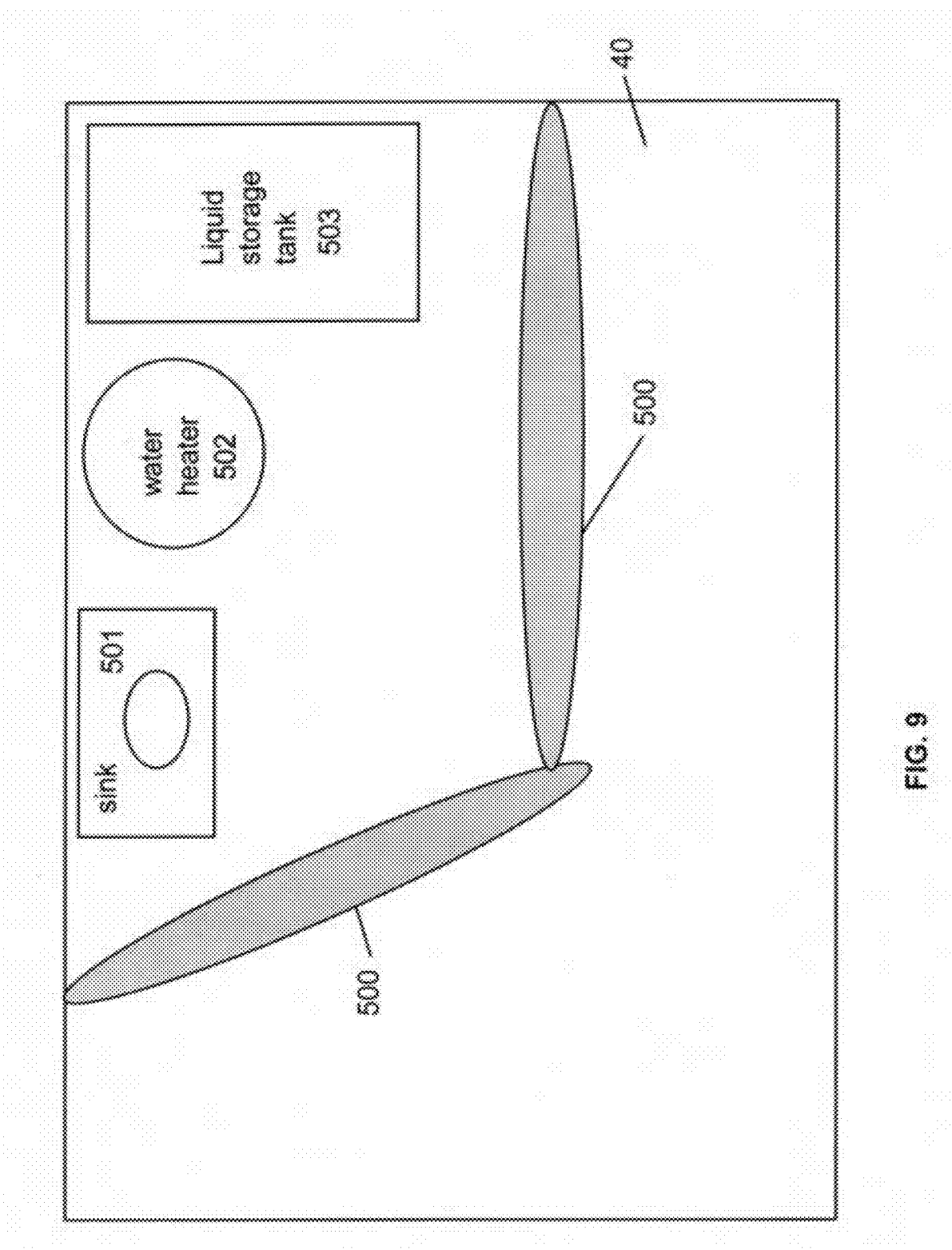
FIG. 9 is an example of a remote surface being monitored by two instances of the source and detector pair in the same housing of the apparatus of FIGS. 1A and 1B in which each source has optics of FIG. 8 providing one linear cross-sectional shaped (thin ellipse) region on the remote surface so as to monitor a perimeter along a remote surface for water.
Figure 10:
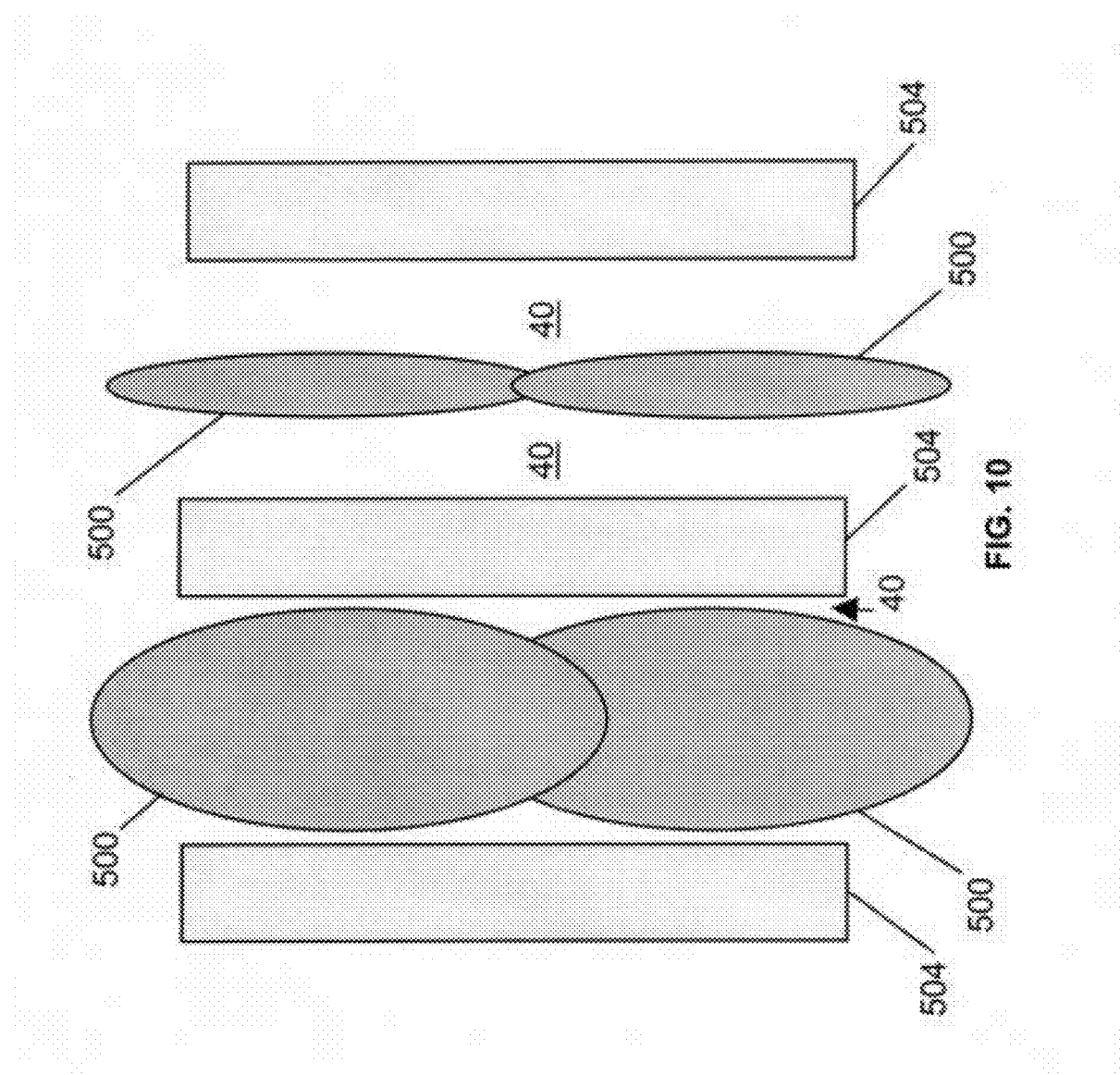
FIG. 10 is an example of a remote surface being monitored by four instances of the source and detector pair in the same housing of the apparatus of FIGS. 1A and 1B in which two of the sources each have the FIG. 8 optics providing a linear (thin ellipses) region on a remote surface and the two other of said source each have optics providing an oval (ellipse) or circular region to show two ways of monitoring an aisle for water.
Figure 11:
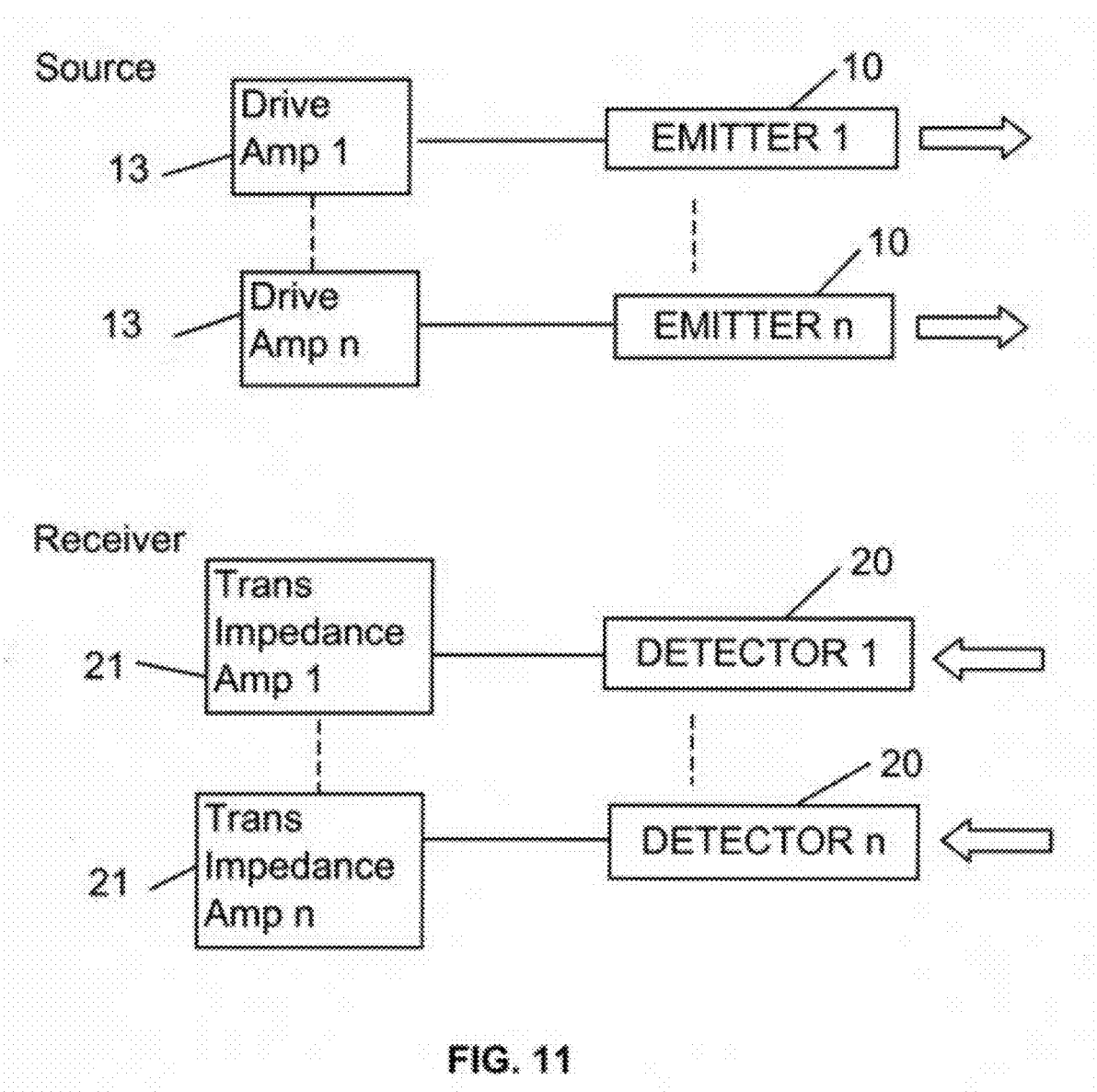
FIG. 11 is a optical diagrammatic view showing the source being provided by multiple light sources of the same or different wavelengths, and multiple detectors which may be utilized in the apparatus of FIGS. 1A and 1B.

In the example of FIG. 9, two asymmetrical elliptical beams 500 may be provided from sources 10 to form a perimeter on surface 40 around devices with the potential for leaks, for example sink 501, water heater 502, liquid storage tank 503. In this case, apparatus 30 has two pairs of sources 10 and detectors 20 in housing 31, each enabling a different analog signal for sampling by controller 100 and operates responsive to the sample data produced as described above. Each source 10 using optics form line beams to form a detection perimeter around three potential leak devices. The advantage of this is that the intensity of the light at the surface is higher, thus allowing greater distance coverage than with a circular beam. The detector cone could likewise be made asymmetrical, but it may not be necessary or cost effective. FIG. 11 as an illustration of the front end electronics 60, having N number sources and detectors, in which N equals two in the example of FIG. 9. FIG. 11 shows a schematic of multiple sources 10 and multiple detectors 20. Emitters 1 . . . N are driven by drive amplifiers 131 . . . N to provide multiple sources. Detectors 1 . . . N detect light and feed current to transimpedance amps 1 . . . N. Each detector provides a different analog signal to controller 100 via components 101, 102 and 110 for sampling and processing by controller 100 as described earlier.

Consider now apparatus 30 having four pairs of sensor 10 and detector 20 in housing 31, each enabling a different analog signal for sampling by controller 100 which operates responsive to the sample data produced as described above. Such apparatus 30 may be used to monitor supermarket aisles for spills as shown for example in the illustration of a remote surface 40 of FIG. 10. In this example, two sets of illumination beams 500 are used to monitor surface 40 in each aisle between the shelves 504. Each of the four sources 10 have optics for enabling the desired beam shape shown in FIG. 10 to adequately cover the area as desired. Again, FIG. 11 is an illustration of the front end electronics 60 having N number sources and detectors, in which N equals four in the example.

Apparatus 30 may also use multiple sources 10 and a single detector 20, where each of multiple sources are at a different IR wavelength and each directing their illumination at different angles at a common region on surface 40. In this case, detector 20 is provided which is sensitive to receiving light in the range of the wavelengths of the multiple sources. Optionally, a separate detector for each one of the multiple sources may be provided where each wavelength source would have a detector corresponding to that particular wavelength (e.g., each of the multiple detectors may have a bandpass filter for a specific wavelength).

Figure 12:
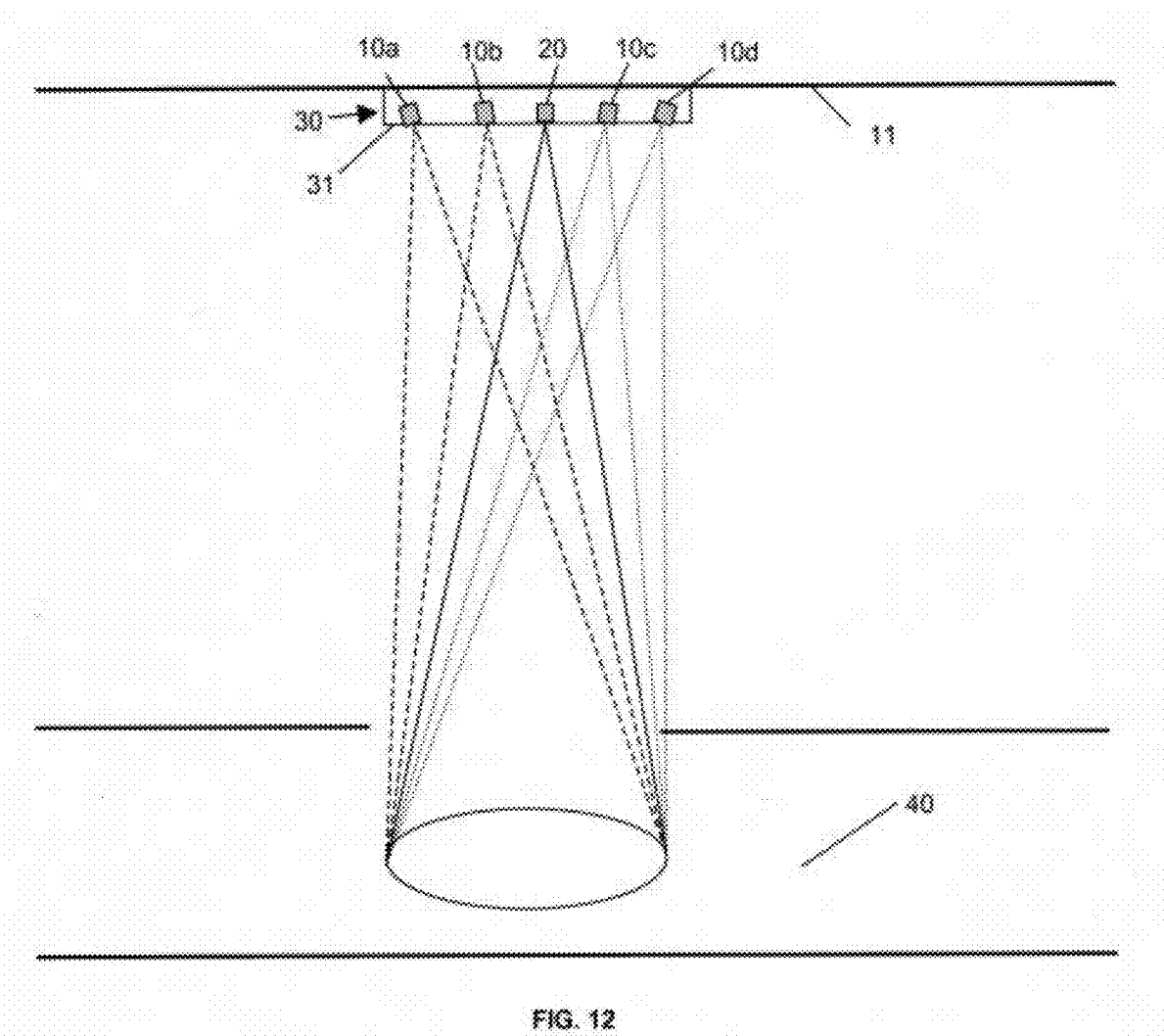
FIG. 12 is an optical diagrammatic view of the apparatus of the present invention having multiple sources operating at different wavelengths of illumination and a single detector.

A single detector is preferable since this reduces overall cost. An example of such an apparatus 30 is shown in FIG. 12 using four sources labeled 10a, 10b, 10c, and 10d and a single detector centrally located between the sources. One advantage of using different wavelengths is that controller 100 can distinguish between one substance and another on surface 40, such as water or oil, as noted previously or to detect multiple substances.

Figure 13A:
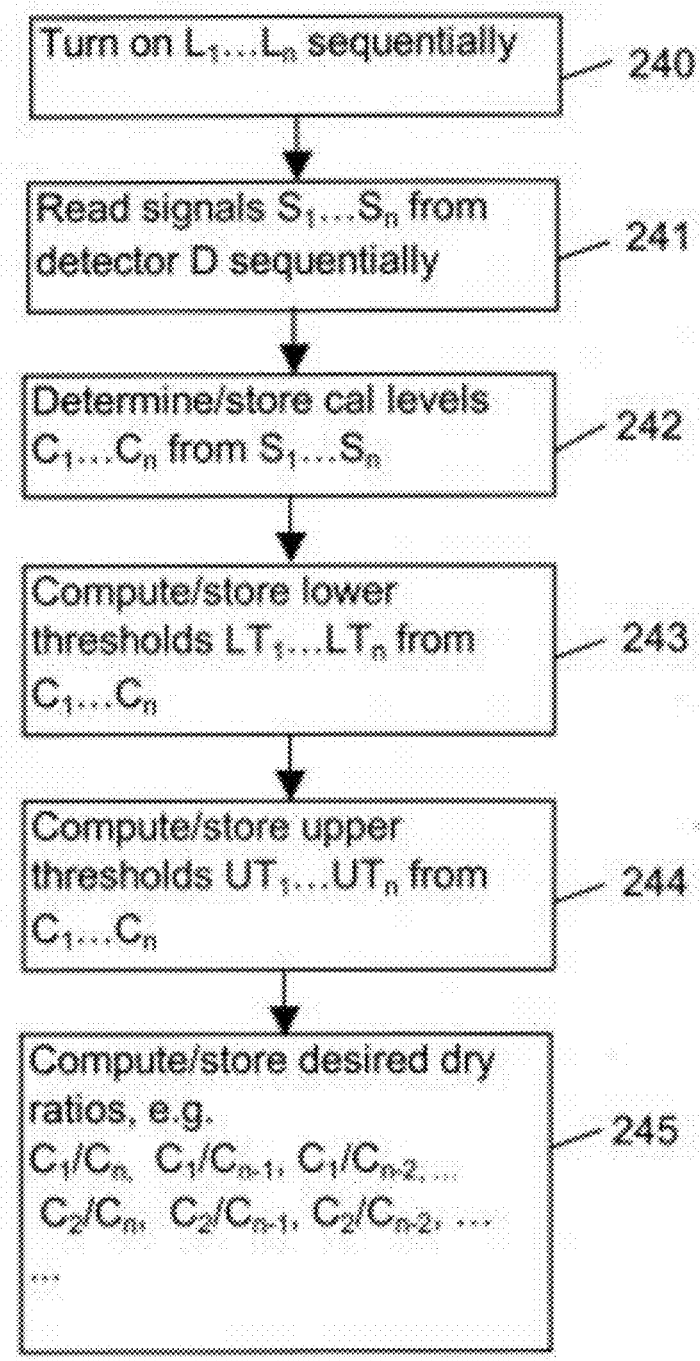
FIG. 13A is flow chart showing the operation in calibration mode of the apparatus of FIG. 12.

A flow chart showing the operation of the controller 100 in a calibration mode in apparatus 30 using sources of multiple wavelengths is shown in FIG. 13A, in which controller 100 separately controls the operation of each source and no substances are present in desired region of detection. Sources are represented by L1 to Ln, where n represents the total number of sources. First, the sources L1 . . . Ln are turned on sequentially by controller 100 (step 240) and the analog signals S1 . . . Sn are sampled sequentially by the controller from detector D 20 (step 241) as each source is separately enabled in the same manner as described previously for a single analog signal. The calibration level for each wavelength is determined, such as described previously, and stored in memory (step 242). A lower threshold for each wavelength is computed and stored in memory (step 243). Then an upper threshold is also computed and stored for each wavelength (step 244). The manner of determining the calibration level and thresholds may be the same as described earlier. The desired ratios for a dry surface are then computed from the calibration levels and stored in memory (step 245). For example, the ratios C1/C3, C4/C2, and C4/C1 may be used, but other ratios may be selected if desired.

Figure 13B:
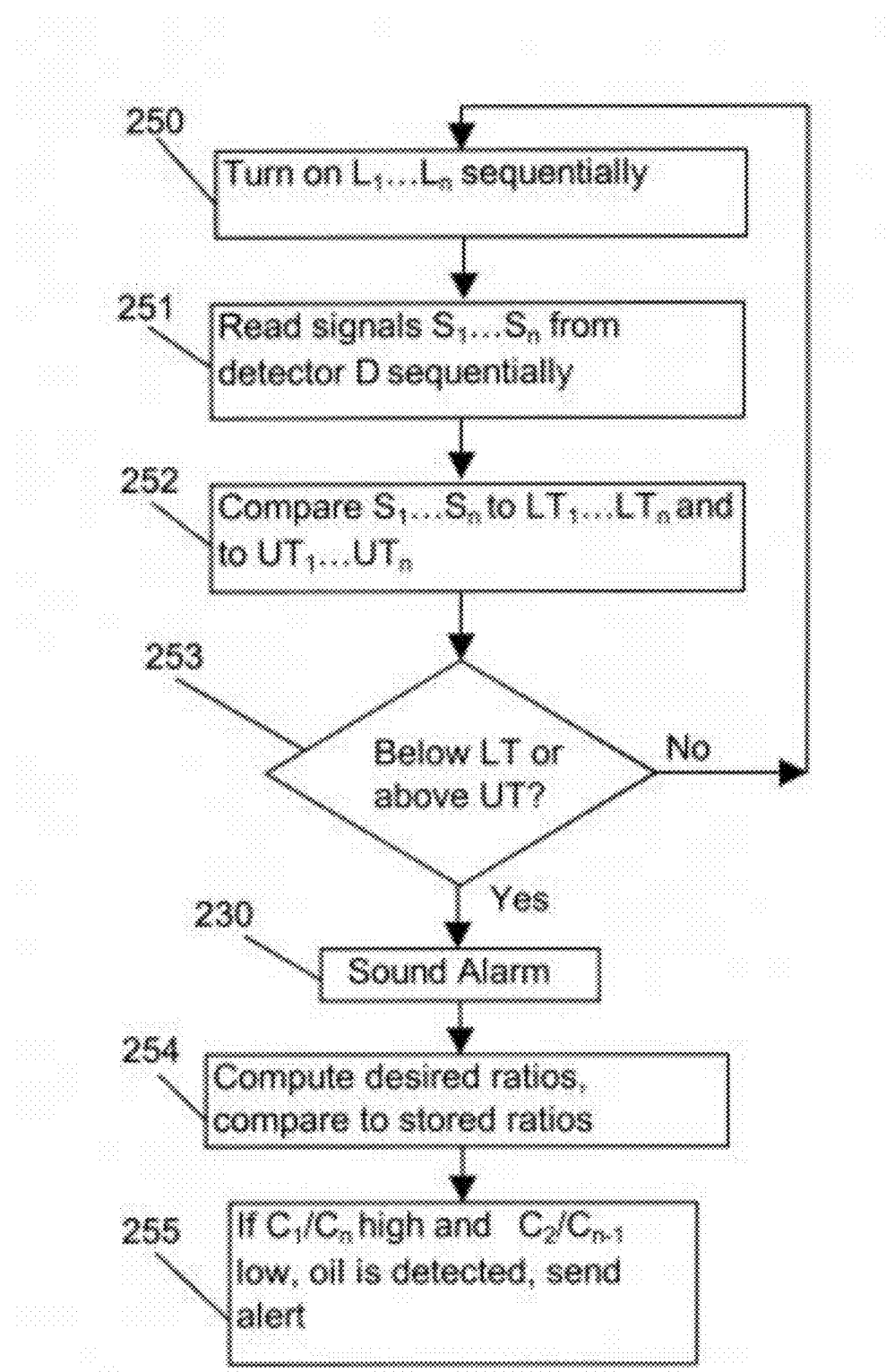
FIG. 13B is flow chart showing the operation in measurement mode of the apparatus of FIG. 12.

A flow chart showing the operation of the controller 100 in a measurement mode in an apparatus 30 using sources of multiple wavelengths is shown in FIG. 13B. The sources 10 L1 . . . Ln are turned on sequentially by controller 100 (step 250) and the analog signals S1 . . . Sn are sampled sequentially by the controller from detector D 20 (step 251) as each source is separately enabled in the same manner as described previously for a single analog signal to provide an average value based on multiple sample values of stored sample data at each wavelength which is compared to that wavelength's stored lower threshold and upper threshold values (step 252). If at none of the wavelengths the average sample data values determined by the controller 100 are at or between their respective lower and upper thresholds, then no possible substances on surface 40 were detected in that measurement mode interval. If at any of the wavelengths the average of the sample data values determined by the controller 100 at the end of a preset measurement interval are above the upper threshold step or below the lower threshold (step 253) then that average sample data value at each wavelength is stored in memory and a detection alarm is sounded to indicated fault condition or a substance detection event, respectively (step 230). The desired ratios are computed by the controller 100 from the stored average sample data value at each wavelength is, now presumably from a wet surface, and these are compared to the stored values for the dry surface (step 254), to determine what type of liquid (or heavy gas, or ice) has been detected (step 255). Such may trigger a local alarm and reported via interface 90 to a security system 131 to others for corrective action to be taken. In the case of the apparatus shown in FIG. 12, in the flowcharts of FIGS. 13A and 13B, n equals four. As an example of step 255, if C1/C3 is high compared to the dry value, and C4/C2 is low compared to its dry value, then an oil leak has been detected and an alert is sent that oil has been detected.

Figure 14:
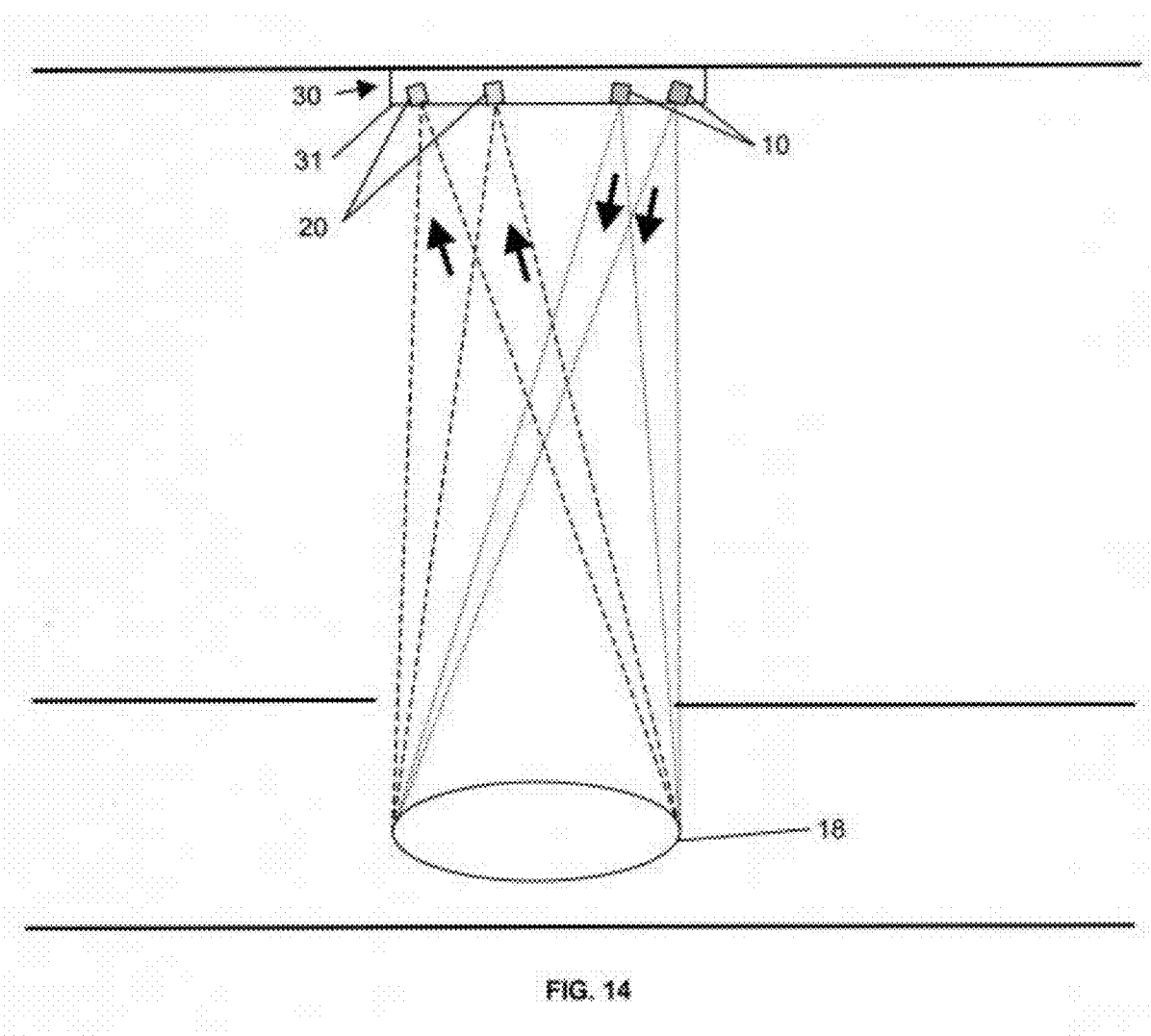
FIG. 14 is a block diagram of the apparatus of the present invention having multiple sources at the same wavelength of illumination, and multiple detectors of equal number to the number of sources, rather than a single source and detector.
Figure 15A:
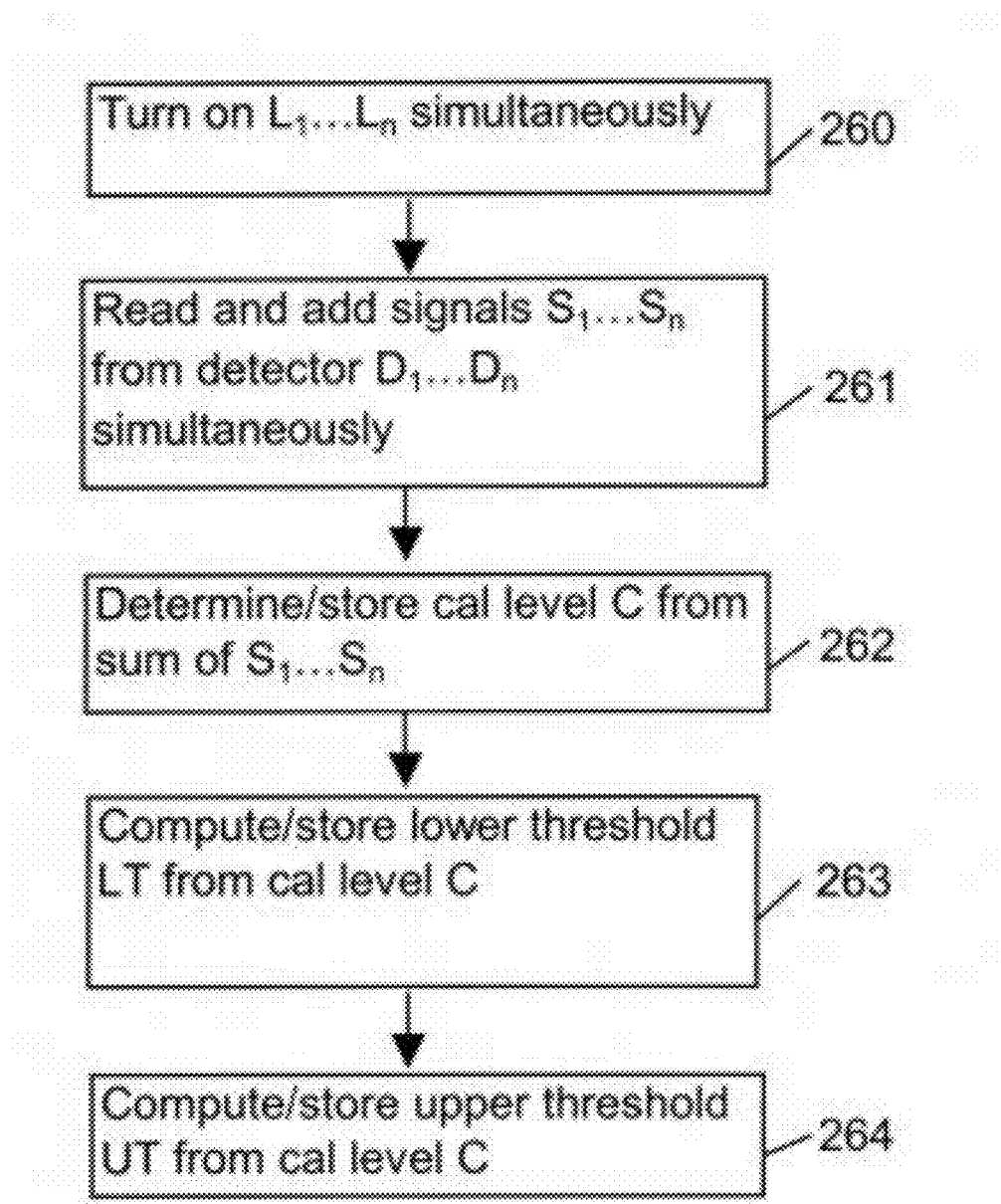
FIG. 15A is flow chart showing the operation in calibration mode of the apparatus of FIG. 14.

Apparatus 30 may also use multiples of sources 10 and multiple detectors 20, where each of multiple sources operate at a same IR wavelength, preferably in the range of 940 nm to 970 nm, to provide more illumination power and more signal strength in the analog signal detected. Such additional power can provide longer working distance, for example, in a warehouse with a high ceiling, such as 20-30 feet. For example, such an apparatus 30 having a housing 31 with two sources operating on the same wavelength, and two detectors is shown in FIG. 14. A flow chart should the operation of the controller 100 in a calibration mode in apparatus 30 using multiple sources of the same wavelengths and multiple detectors is shown in FIG. 15A, in which controller 100 separately controls the operation of each source and no water (or moisture) is present in desired region of detection. Sources are represented by L1 to Ln, detectors are represented by D1 to Dn, where n represents the total number of source detector pairs (i.e., L1,D1; L2,D2, to Ln,Dn) in housing 31. The sources are turned on simultaneously by controller 100 (step 260) and the analog signals S1 . . . Sn from the detectors D1 . . . Dn are sampled by the controller which then adds the sampled values at each capture time together (step 261) to obtain a larger sample value. Multiple sample values are stored as sample data, the average of which provides a calibration level which is stored (step 262). A lower threshold (step 263) and an upper threshold (step 264) are then computed by the controller 100 from the calibration level. The manner of determining the calibration level and threshold may be the same as described earlier.

Figure 15B:
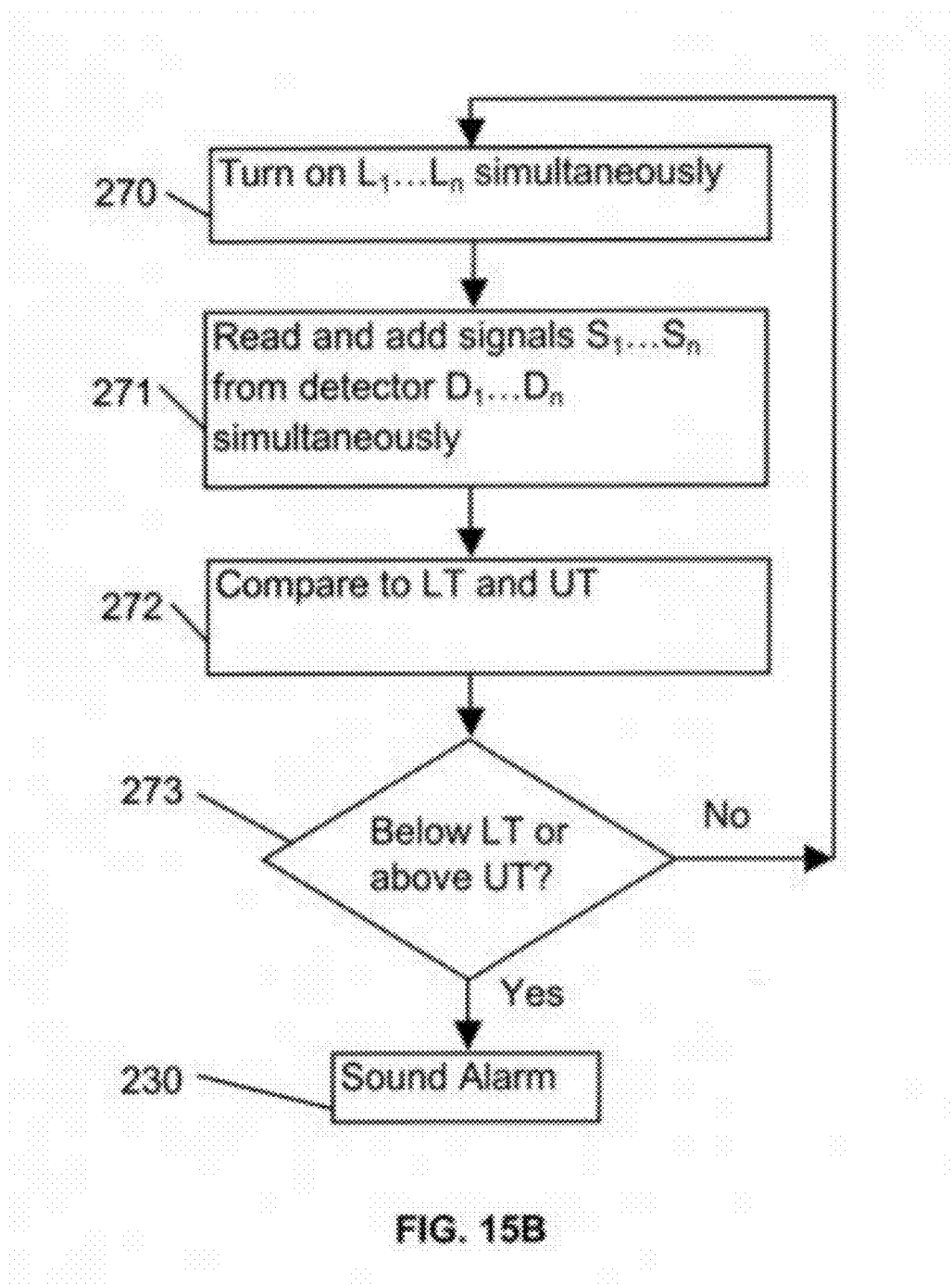
FIG. 15B is flow chart showing the operation in measurement mode of the apparatus of FIG. 14.

A flow chart showing the operation of the controller 100 in a measurement mode in an apparatus 30 using multiple sources of the same wavelength and multiple detectors is shown in FIG. 15B. All the sources are turned on simultaneously by controller 100 (step 270), and the analog signals S1 . . . Sn from the detectors D1 . . . Dn are sampled by the controller which then adds the sampled values at each capture time together to obtain a larger sample value (step 271). A number N of such larger sample values, e.g., N=10, are stored in memory as sample data, averaged, and then compared to the lower and upper thresholds by the controller (step 272), and if such average value is not below the lower threshold or above the upper threshold (i.e., normal range) at step 273 then steps 270-273 are repeated, otherwise an alarm is triggered by controller 100 to indicate a fault condition or a water detection event, respectively (step 230).

Using same wavelength sources mounted at differing incident angles as shown in FIG. 14 for example (and/or sources 10 operating at different modulation frequencies via signals from oscillator 105 via driver amplifier 13) allow greater information about the surface being viewed. For example, five sources 10 can be provided in housing 31 at the following angles, perpendicular to the floor 40 (at or about 0 degrees), at +5°, −5°, +10°, and −10° from the perpendicular to the floor 40. Software in memory 121 enables digital controller 100 to compare sample values (or averages thereof) from each of detectors 20, and ratios of sample values (or averages thereof), from all the detectors and determine whether to give more weight to certain sampled analog signals than others. For example, if the source pointing perpendicular to the floor 40 is associated with a measured sample value (or average value of multiple sample values) above the calibration level, then it is likely receiving a specular reflection and should be ignored. Meanwhile, the other 4four sampled analog signals having sample values (or averages thereof) below the lower threshold are indicating water detection. Most likely, a sheet of water has covered the floor and is causing a specular reflection into the perpendicular beam detector.

Although the housing 31 is described as being mounted on a surface in a home or building, the housing could be mounted on surfaces outside a building to detect ice, for example on a sidewalk or staircase. Alarm indicating ice can alert employers, apartment managers, or others to take slip prevention measures. To detect the presence of other substances than water upon a remote surface, such as oil or alcohol, frozen liquids such as ice, and gases such as water vapor as a mist and heavy gases, the same apparatus 30 may be used so long as such substances results in a measurable reduction in return light from surface 40 similar to the detection of water as described above.

From the foregoing description, it will be apparent that an improved apparatus and method for detecting the presence of water on a remote surface has been provided, which may also be used to detect the presence of other substances than water upon a remote surface, such as oil or alcohol, frozen liquids such as ice, and gases such as water vapor as a mist and heavy gases. Variations and modifications in the herein described apparatus and method will undoubtedly become apparent to those skilled in the art. Accordingly, the foregoing description should be taken as illustrative and not in a limiting sense.

The invention claimed is:

1. An apparatus for detecting a substance upon a surface comprising:
    a source configured to illuminate a surface with at least one wavelength of light, wherein the source is configured to be driven at an oscillation frequency to modulate the illumination from the source;
    a receiver configured to receive returned illumination from the surface;
    a synchronous detector that provides a signal representative of the received returned illumination in accordance with the oscillation frequency that modulated the source; and
    a controller configured to sample the signal at a time in accordance with the oscillation frequency to minimize the effect of any ambient light received by the synchronous detector in the signal to obtain sample data representative of amplitude of light of the source returned from the surface, and the controller determines the presence of the substance, on the surface in accordance with the sample data.

2. The apparatus according to claim 1 wherein the oscillation frequency has alternating peaks of a different sign (+ and -), and the controller determines each time the signal corresponds to when the source was driven at the peaks and samples the signal at each of the times to obtain the sample data representative of the amplitude of the signal.

3. The apparatus according to claim 2 wherein the sample data for each sample of the signal represents an absolute value of the difference of the amplitude of the signal when sampled and the amplitude of the signal when previously sampled.

4. The apparatus according to claim 1 further comprising a quadrature detector configured to determine the difference in phase between the oscillation frequency of the source and the detected oscillation frequency of the return signal, and the sampling by the controller detector is offset by the difference in phase.

5. The apparatus according to claim 4 wherein the quadrature detector is part of the controller.

6. The apparatus according to claim 1 wherein the controller determines the presence of the substance in accordance with the sample data having a representative value in a period of time below a first threshold value, and the controller determines a fault condition in accordance with the sample data having a representative value in a period of time above a second threshold value, in which the fault condition prevents detection of the substance by the controller.

7. The apparatus according to claim 6 further comprising memory, wherein the controller stores sample data in the memory, and determines the presence of the substance in accordance with an average value of a plurality of the sample data stored in said memory over a period of time being below the first threshold to avoid false detection of the substance by the controller.

8. The apparatus according to claim 6 wherein the illumination is projected by the source along a first direction to illuminate a first region along the surface, and the receiver receives returned illumination along a second direction from a second region along the surface, in which the first region and the second region are the same or substantially overlap along the surface and wherein the first and second thresholds are set by the controller in accordance with sample data when the first region and second region along the surface is dry.

9. The apparatus according to claim 1 wherein the source is an LED operative at a wavelength in a range of 940 nm to 970 nm.

10. The apparatus according to claim 1 wherein the receiver comprises a phototransistor, photodiode, an avalanche photodiode, a photomultiplier, or LED for use as an illumination receiving element for detecting the returned illumination.

11. The apparatus according to claim 1 further comprising an audible alarm which is activated by the controller when the controller determines the presence of the substance on the surface.

12. The apparatus according to claim 1 wherein the controller is configured to control the operation of the source, the controller operates in at least a measurement mode and a sleep mode, the source is enabled by the controller in the measurement mode, the source is disabled by the controller in the sleep mode, and the controller alternates between the measurement mode and sleep mode.

13. The apparatus according to claim 12 wherein the controller operates in the sleep mode for a first period of time, and when the controller determines the presence of the substance in accordance with the sample data during the measurement mode the controller operates in the sleep mode for a second period to time shorter than the first period of time to increase the rate the controller alternates between the measurement mode and sleep mode.

14. The apparatus according to claim 13 wherein after a certain number of alternating periods of the measurement mode and the sleep mode at the increased rate the controller has determined the presence of the substance in accordance with the sample data, the controller activates an alarm indicative of the presence of the substance on the surface, otherwise the controller reset the sleep mode to the first period of time.

15. The apparatus according to claim 1 further comprising first optics for directing the illumination from the source to the surface.

16. The apparatus according to claim 15 wherein the first optics comprise one or more of a parabolic reflector, a lens, or a filter.

17. The apparatus according to claim 15 wherein the first optics comprises one or more of a glass lens, a molded plastic lens, a Fresnel lens, a cylinder lens, or a prism.

18. The apparatus according to claim 15 wherein the first optics comprises one or more cylinder lenses or prisms for forming a line beam on the surface.

19. The apparatus according to claim 15 further comprising second optics for collecting return light from the surface to the detector, and the second optics are identical to the first optics.

20. The apparatus according to claim 1 further comprising one or more optical elements for filtering illumination from one or more of the source and the detector.

21. The apparatus according to claim 1 wherein the source represents a plurality of sources each providing illumination at the same or different wavelengths.

22. The apparatus according to claim 21 wherein the sources are at different angles with respect to each other.

23. The apparatus according to claim 1 wherein the source represents a plurality of sources of a plurality of different wavelengths, and the synchronous detector providing the signal which is sampled by the controller to provide sample data for each one of the plurality of wavelengths.

24. The apparatus according to claim 23 wherein the controller determines a ratio of two values each representative of sample data associated with a different one of the plurality of wavelengths to determine the condition and type of fluid on the surface.

25. The apparatus according to claim 1 further comprising:
a housing for at least the source, the detector, and the controller, the housing is at a distance from the surface;
the illumination is projected by the source from the housing along a first direction to illuminate a first region along the surface, and the detector receives return illumination at the housing along a second direction from a second region along the surface, in which the first region and the second region are the same or substantially overlap along the surface; and
the synchronous detector is operable to provide the signal enabling the controller to obtain the sample data for use in determining the presence of the substance on the surface when the first direction and the second direction are each perpendicular with respect to the surface and when the first direction and the second direction are each non-perpendicular with respect to the surface.

26. The apparatus according to claim 25 wherein the surface represents a first surface, and the housing is mounted on a second surface at the distance from the first surface.

27. The apparatus according to claim 26 wherein the first surface represents the surface of a floor of a building or room, and the second surface represents the wall or ceiling of the building, room, or basement.

28. The apparatus according to claim 25 further comprising a visible LED or visible laser pointer used to align the first direction and second direction at a location on the surface.

29. The apparatus according to claim 1 wherein the substance comprises moisture, liquid, ice, vapor or heavy gases.

30. A method for detecting of a substance on a surface comprising:
   illuminating a surface with at least one wavelength of light along a first direction to the surface in which the source is driven at an oscillation frequency;
   receiving at a receiver returned illumination from the surface;
   providing with a synchronous detector and in accordance with the oscillation frequency a signal representative of the received returned illumination; and
   sampling by a controller the signal at a time in accordance with the oscillation frequency to minimize the effect of any ambient light received by the synchronous detector to obtain sample data representative of amplitude of light of the source returned from the surface; and
   determining the presence of the substance in accordance with the sample data.

31. The method according to claim 30 further comprises providing an alarm signal when the presence of the substance is determined.

32. The method according to claim 30 wherein the determining step further comprising:
   determining in accordance with a first threshold when the sample data indicates the presence of the substance; and
   determining in accordance with a second threshold when the apparatus is in a condition preventing detection of the substance.

33. The method according to claim 30 wherein the illuminating further comprises providing illumination in the range of 940 to 970 nm.

34. The method according to claim 30 wherein the substance comprises moisture, liquid, ice, vapor or heavy gases.

35. An apparatus for detecting a substance upon a surface comprising:
   a source configured to illuminate the surface with at least one wavelength of light, wherein the source is configured to be driven at an oscillation frequency to modulate the illumination from the source;
   a receiver configured to receive returned illumination from the surface illuminated by the source;
   a synchronous detector that provides a signal representative of the received returned illumination in accordance with the oscillation frequency that modulated the source; and
   a controller configured to sample the signal at a time in accordance with the oscillation frequency to minimize the effect of any ambient light to obtain sample data representative of amplitude of light of the source returned from the surface, and determines in accordance with a first threshold when the sample data indicates the presence of the substance, and determines in accordance with a second threshold when the sample data indicates a fault condition preventing detection of the substance.

36. The apparatus according to claim 35 wherein the substance comprises moisture, liquid, ice, vapor or heavy gases.

37. An apparatus for detecting a substance upon a surface comprising:
   a source configured to illuminate the surface with at least one wavelength of light in which the source is driven at an oscillation frequency to modulate the illumination from the source;
   a receiver configured to receive returned illumination from the surface;
   a synchronous detector that provides a signal representative of the received returned illumination in accordance with the oscillation frequency that modulated the source; and
   a controller configured to sample the signal at a time in accordance with the oscillation frequency to minimize the effect of any ambient light received to obtain sample data representative of amplitude of light of the source returned from the surface in which the time of capture of each sample of the signal by the controller is in accordance with the synchronous detector aligned with the peaks of the oscillation frequency by a quadrature detector to diminish effect of any ambient light present in the signal; and
   the controller determines the presence of the substance in accordance with the sample data.

38. The apparatus according to claim 37 wherein the substance comprises moisture, liquid, ice, vapor or heavy gases.

39. An apparatus for detecting the substance upon a surface comprising:
   a source configured to illuminate the surface with at least one wavelength of light wherein the source is configured to be driven at an oscillation frequency to modulate the illumination from the source;
   a receiver configured to receive returned illumination from the surface;
   a synchronous detector that provides a signal representative of the received returned illumination in accordance with the oscillation frequency that modulated the source; and
   a controller configured to sample the signal at a time in accordance with the oscillation frequency to minimize the effect of any ambient light received to obtain sample data representative of amplitude of light of the source returned from the surface; and
   the controller controls the operation of the source and the synchronous detector, the controller operates in at least a measurement mode and a sleep mode, the source is enabled by the controller in the measurement mode for a first period of time, the source is disabled by the controller in the sleep mode for a second period of time, the controller alternates between the measurement mode and sleep modes, the first time period is less than the second time period, and the second period of time is automatically adjusted to increase the frequency of the controller in the measurement mode upon controller determination of possible the substance in accordance with the sample data in order to verify the presence of the substance on the surface.

40. The apparatus according to claim 39 wherein the substance comprises moisture, liquid, ice, vapor or heavy gases.

* * * * *